United States Patent
Ruoslahti et al.

[11] Patent Number: 5,837,813
[45] Date of Patent: *Nov. 17, 1998

[54] FIBRONECTIN TYPE III POLYPEPTIDES

[75] Inventors: Erkki I. Ruoslahti, Rancho Santa Fe; Alex Morla, Carlsbad, both of Calif.

[73] Assignee: La Jolla Cancer Research Foundation, La Jolla, Calif.

[*] Notice: The term of this patent shall not extend beyond the expiration date of Pat. No. 5,453,489.

[21] Appl. No.: 460,421

[22] Filed: Jun. 1, 1995

Related U.S. Application Data

[63] Continuation of Ser. No. 340,812, Nov. 17, 1994, Pat. No. 5,629,291, which is a continuation of Ser. No. 21,626, Feb. 16, 1993, abandoned, which is a continuation-in-part of Ser. No. 829,462, Jan. 31, 1992, Pat. No. 5,453,489.

[51] Int. Cl.$^6$ .............................. A61K 38/39; C07K 14/78
[52] U.S. Cl. .......................... 530/350; 530/324; 530/380; 530/395
[58] Field of Search .............................. 530/350; 435/69.1

[56] References Cited

U.S. PATENT DOCUMENTS

| | | | |
|---|---|---|---|
| 4,578,079 | 3/1986 | Ruoslahti et al. | 623/11 |
| 4,589,881 | 5/1986 | Pierschbacher et al. | 623/11 |
| 4,980,279 | 12/1990 | Peters et al. | 435/7 |
| 5,108,898 | 4/1992 | Peters et al. | 435/7.9 |
| 5,453,489 | 9/1995 | Ruoslahti et al. | 530/350 |
| 5,492,890 | 2/1996 | Ginsgerg et al. | 514/12 |

FOREIGN PATENT DOCUMENTS

| | | |
|---|---|---|
| 035202 A2 | 9/1981 | European Pat. Off. . |
| 207751-A | 1/1987 | United Kingdom . |

OTHER PUBLICATIONS

Bowie et al. Deciphering the message in protein sequences: tolerance to amino acid substitutions. Science, vol. 247, 1306–1310, Mar. 1990.

Akiyama et.al., Analysis of Fibronectin Receptor Function with Monoclonal Antibodies: Roles in Cell Adhesion, Migration, Matrix Assembly, and Cytoskeletal Organization. J. Cell Biol., 109: 863–875 (1991).

Ali and Hynes, Role of Disulfide Bonds in the Attachment and Function of Large, External, Transformation–Sensitive Glycoprotein at the Cell Surface. Biochim. Biophys. Acta. 510:140–150 (1978).

Chernousov et.al., Role of I–9 and III–1 Modules of Fibronectin in Formation of an Extracellular Fibronectin Matrix. J. Biol. Chem. 266: 10851–10858 (1991).

Ehrismann et al., Mode of Action of Fibronectin in Promoting Chicken Myoblast Attachment. Mr=60,000 gelatin–binding fragment binds native fibronectin. J. Biol. Chem. 256:4056–4062 (1981).

Ehrismann et al., Arrangement of Attachment–Promoting, Self–Association, and Heparin–Binding Sites in Horse Serum fibronectin. J. Biol. Chem. 257: 7381–7387 (1982).

(List continued on next page.)

*Primary Examiner*—Stephen Walsh
*Assistant Examiner*—David S. Romeo
*Attorney, Agent, or Firm*—Campbell & Flores LLP

[57] ABSTRACT

The present invention provides fibronectin self-assembly sites. The invention provides a set of polypeptides derived from the first type III repeat of fibronectin which contain a fibronectin-fibronectin binding site. These polypeptides have been used to obtain a second set of polypeptides derived from the C-terminal type I repeats which contain a second fibronectin-fibronectin binding site which interacts with the first type III repeat of fibronectin. These polypeptides are capable of inhibiting fibronectin matrix assembly by interfering with fibronectin-fibronectin binding. These polypeptides are also capable of enhancing fibronectin matrix assembly and inducing disulfide cross-linking of fibronectin molecules in vitro. In addition, these polypeptides are capable of inhibiting migration of tumor cells. The polypeptides of the present invention have a number of related uses as well.

4 Claims, 21 Drawing Sheets

OTHER PUBLICATIONS

Fogerty et al., Inhibition of Binding of Fibronectin to Matrix Assembly Sites by Anti–integrin (alpha 5 beta 1) Antibodies. J. Cell. Biol. 111: 699–708 (1990).

Giancotti and Ruoslahti, Elevated Levels of the Alpha 5 Beta 1 Fibronectin Receptor Suppress the Transformed Phenotype of Chinese Hamster Ovary Cells. Cell 60: 849–859 (1990).

Hynes and Destree, Extensive Disulfide Bonding at the Mammalian Cell Surface. Proc. Natl. Acad. Sci. U.S.A. 74:2855–2859 (1977).

Keski–Oja et al., Dimeric Character of Fibronectin, a Major Cell Surface–Associated Glycoprotein. Biochem. Biophys. Res. Commun. 74: 699–706 (1977).

McDonald, J.A., Extracellular Matrix Assembly. Annu. Rev. Cell Biol. 4: 183–207 (1988).

McDonald et.al., Fibronectin Cell–Adhesive Domain and an Amino–Terminal Matrix Assembly Domain Participate in it Assembly into Fibroblast Pericellular Matrix. J. Biol. Chem. 262: 2957–2967 (1987).

McKeown–Longo et.al., Interaction of the 70,000–mol–wt Amino–terminal Fragment of Fibronectin with the Matrix–assembly Receptor of Fibroblasts. J. Cell Biol. 100: 364–374 (1985).

Mosher et.al., Assembly of Fibronectin into Extracellular Matrix. Ann. N.Y. Acad. Sci. 614:167–180 (1991).

Nagai et.al., Monoclonal Antibody Characterization of Two Distant Sites Required for Function of the Central Cell–Binding Domain of Fibronectin in Cell Adhesion, Cell Migration, and Matrix Assembly. J. Cell Biol. 114: 1295–1305 (1991).

Oh et.al., Deposition of Plasma Fibronectin in Tissues. Prod. Natl. Acad. Sci. U.S.A. 78: 3218–3221 (1981).

Peters and Mosher, Localization of Cell Surface Sites Involved in Fibronectin Fibrillogenesis. J. Cell Biol. 104: 121–130 (1987).

Peters et.al., Co–assembly of Palsma and Cellular Fibronectins into Fibrils in Human Fibroblast Cultures. J. Cell Biol. 111: 249–256 (1990).

Pierschbacher et.al., Cell Attachment Activity of Fibronectin can be Duplicated by Small Synthetic Fragments of the Molecule. Nature 309: 30–33 (1984).

Pierschbacher et.al., Synthetic Peptide with Cell Attachment Activity of Fibronectin. Proc. Natl. Acad. Sci. U.S.A. 80: 1224–1227 (1983).

Pierschbacher et.al., Variants of the Cell Recognition Site of Fibronectin That Retain Attachment–promoting Activity. Proc. Natl. Acad. Sci. U.S.A. 81: 5985–5988 (1984).

Pytela et.al., Identification and Isolation of a 140 kd Cell Surface Glycoprotein with Properties Expected of a Fibronectin Receptor. Cell 40: 191–198 (1985).

Quade and McDonald, Fibronectin's Amino–terminal Matrix Assembly Site is Located Within the 29–kDa Amino–terminal Domain Containing Five Type I Repeats. J. Biol. Chem. 263: 19602–19609 (1988).

Ruoslahti, E., Fibronectin and its Receptors. Annu. Rev. Biochem. 57: 375–413 (1988).

Ruoslahti, E., Integrins. J. Clin. Invest. 87:1–5 (1991).

Schwarzbauer, J.E., Identification of the Fibronectin Sequences Required for assembly of a Fibrillar Matrix. J. Cell Biol. 113: 1463–1473 (1991).

Schwarzbauer, et al., Efficient and Stable Expression of Recombinant Fibronectin Polypeptides. Proc. Natl. Acad. Sci. U.S.A. 84: 754–758 (1987).

Woods et.al., Fibronectin Fibril Formation Involves Cell Interactions With Tow Fibronectin Domains. Exp. Cell Res. 177: 272–283 (1988).

Calaycay, J. et al., *J. Biol. Chem.* 260:12136–12141 (1985).

Hayashi, M. et al., *J. Biol. Chem.* 256:11292–112300 (1981).

Morla, et al., "A Fibronectin self–Assembly Site Involved in Fibronectin Matrix Assembly: Reconstruction in a Synthetic Peptide." *J. Cell Biol.* 118(2): 421–429 (1992).

Engvall and Ruoslahti, *Int. J. Cancer* 20:1–5 (1977).

Kornblihtt et al., *EMBO J.* 4:1755–1759 (1985).

Gearing et al., *Bio/Technology* 7:1157 (1989).

Smith et al., *Gene* 67:31–40 (1988).

McKeown–Longo and Mosher, *J. Cell Biol.* 97: 466–472 (1983).

Hormann and Richter, *Biopolymers* 25:947–958 (1986).

Homandberg and Erickson, *Biochemistry* 25:6917–6925 (1986).

Homandberg, G.A., *Biopolymers* 26:2087–2098 (1987).

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asn Ala Pro Gln Pro Ser His Ile Ser Lys Tyr Ile Leu Arg Trp Arg
 1               5                  10                  15
Pro Lys Asn Ser Val Gly Arg Trp Lys Glu Ala Thr Ile Pro Gly His
            20                  25                  30
Leu Asn Ser Tyr Thr Ile Lys Gly Leu Lys Pro Gly Val Val Tyr Glu
        35                  40                  45
Gly Gln Leu Ile Ser Ile Gln Gln Tyr Gly His Gln Glu Val Thr Arg
    50                  55                  60
Phe Asp Phe Thr Thr Thr Ser Thr Ser Thr Pro Val Thr Ser Asn Thr
65                  70                  75                  80
Val Thr Gly Glu Thr Thr Pro Phe Ser Pro Leu Val Ala Thr Ser Glu
                85                  90                  95
Ser Val Thr Glu Ile Thr Ala Ser Ser Phe Val Val Ser
                100                 105
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Asn Ala Pro Gln Pro Ser His Ile Ser Lys Tyr Ile Leu Arg Trp Arg
 1               5                  10                  15
Pro Lys Asn Ser Val Gly Arg Trp Lys Glu Ala Thr Ile Pro Gly
            20                  25                  30
```

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Glu Ala Thr Ile Pro Gly His Leu Asn Ser Tyr Thr Ile Lys Gly Leu
 1               5                  10                  15
Lys Pro Gly Val Val Tyr Glu Gly Gln Leu Ile Ser Ile Gln Gln
            20                  25                  30
```

( 2 ) INFORMATION FOR SEQ ID NO:4:

( i ) SEQUENCE CHARACTERISTICS:

(A) LENGTH: 31 amino acids
(B) TYPE: amino acid
(D) TOPOLOGY: linear (ii) MOLECULE TYPE: peptide (xi) SEQUENCE DESCRIPTION: SEQ ID NO:4:

Leu Ile Ser Ile Gln Gln Tyr Gly His Gln Glu Val Thr Arg Phe Asp
1               5                   10                  15
Phe Thr Thr Thr Ser Thr Ser Thr Pro Val Thr Ser Asn Thr Val
            20                  25                  30

(2) INFORMATION FOR SEQ ID NO:5:

(i) SEQUENCE CHARACTERISTICS:
    (A) LENGTH: 34 amino acids
    (B) TYPE: amino acid
    (D) TOPOLOGY: linear (ii) MOLECULE TYPE: peptide (xi) SEQUENCE DESCRIPTION: SEQ ID NO:5:

Val Thr Ser Asn Thr Val Thr Gly Glu Thr Thr Pro Phe Ser Pro Leu
1               5                   10                  15
Val Ala Thr Ser Glu Ser Val Thr Glu Ile Thr Ala Ser Ser Phe Val
            20                  25                  30
Val Ser (2) INFORMATION FOR SEQ ID NO:6:

(i) SEQUENCE CHARACTERISTICS:
    (A) LENGTH: 44 amino acids
    (B) TYPE: amino acid
    (D) TOPOLOGY: linear (ii) MOLECULE TYPE: peptide (xi) SEQUENCE DESCRIPTION: SEQ ID NO:6:

Arg Trp Ser His Asp Asn Gly Val Asn Tyr Lys Ile Gly Glu Lys Trp
1               5                   10                  15
Asp Arg Gln Gly Glu Asn Gly Gln Met Met Ser Ser Thr Ser Leu Gly
            20                  25                  30
Asn Gly Lys Gly Glu Phe Lys Ser Asp Pro His Glu
            35                  40

(2) INFORMATION FOR SEQ ID NO:7:

(i) SEQUENCE CHARACTERISTICS:
    (A) LENGTH: 42 amino acids
    (B) TYPE: amino acid
    (D) TOPOLOGY: linear (ii) MOLECULE TYPE: peptide (xi) SEQUENCE DESCRIPTION: SEQ ID NO:7:

Ala Thr Ser Tyr Asp Asp Gly Lys Thr Tyr His Val Gly Glu Gln Trp
1               5                   10                  15
Gln Lys Glu Tyr Leu Gly Ala Ile Ser Ser Thr Ser Phe Gly Gly
            20                  25                  30
Gln Arg Gly Trp Arg Ser Asp Asn Ser Arg
            35                  40

(2) INFORMATION FOR SEQ ID NO:8:

(i) SEQUENCE CHARACTERISTICS:

( A ) LENGTH: 27 base pairs
          ( B ) TYPE: nucleic acid
          ( C ) STRANDEDNESS: single
          ( D ) TOPOLOGY: linear ( i i ) MOLECULE TYPE: DNA (genomic)

( i x ) FEATURE:
          ( A ) NAME/KEY: misc_feature
          ( B ) LOCATION: 1..27
          ( D ) OTHER INFORMATION: /note= "SYNTHETIC PRIMER, NOT
                GENOMIC"

( x i ) SEQUENCE DESCRIPTION: SEQ ID NO:8:

CCGGATCCAA TGCACCACAG CCATCTC 27

( 2 ) INFORMATION FOR SEQ ID NO:9:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: DNA (genomic)

( i x ) FEATURE:
          ( A ) NAME/KEY: misc_feature
          ( B ) LOCATION: 1..27
          ( D ) OTHER INFORMATION: /note= "SYNTHETIC PRIMER, NOT
                GENOMIC"

( x i ) SEQUENCE DESCRIPTION: SEQ ID NO:9:

CCGGATCCCT GCTGGATGCT GATGAGC 27

( 2 ) INFORMATION FOR SEQ ID NO:10:

( i ) SEQUENCE CHARACTERISTICS:
          ( A ) LENGTH: 28 base pairs
          ( B ) TYPE: nucleic acid
          ( C ) STRANDEDNESS: single
          ( D ) TOPOLOGY: linear ( i i ) MOLECULE TYPE: DNA (genomic)

( i x ) FEATURE:
          ( A ) NAME/KEY: misc_feature
          ( B ) LOCATION: 1..28
          ( D ) OTHER INFORMATION: /note= "SYNTHETIC PRIMER, NOT
                GENOMIC"

( x i ) SEQUENCE DESCRIPTION: SEQ ID NO:10:

CCGGATCCAG GTGTGCTGGT GCTGGTGG 28

( 2 ) INFORMATION FOR SEQ ID NO:11:

( i ) SEQUENCE CHARACTERISTICS:
          ( A ) LENGTH: 85 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:11:

```
Gly Ser Asn Ala Pro Gln Pro Ser His Ile Ser Lys Tyr Ile Leu Arg
1               5                   10                  15

Trp Arg Pro Lys Asn Ser Val Gly Arg Trp Lys Glu Ala Thr Ile Pro
            20                  25                  30

Gly His Leu Asn Ser Tyr Thr Ile Lys Gly Leu Lys Pro Gly Val Val
        35                  40                  45
```

```
Tyr Glu Gly Gln Leu Ile Ser Ile Gln Gln Tyr Gly His Gln Glu Val
    50                  55                  60

Thr Arg Phe Asp Phe Thr Thr Thr Ser Thr Ser Thr Pro Gly Ser Pro
65              70                  75                      80

Gly Ile His Arg Asp
                85
```

(2) INFORMATION FOR SEQ ID NO:12:

(i) SEQUENCE CHARACTERISTICS:
        (A) LENGTH: 66 amino acids
        (B) TYPE: amino acid
        (D) TOPOLOGY: linear (ii) MOLECULE TYPE: peptide (xi) SEQUENCE DESCRIPTION: SEQ ID NO:12:

```
Gly Ser Asn Ala Pro Gln Pro Ser His Ile Ser Lys Tyr Ile Leu Arg
1               5                   10                  15

Trp Arg Pro Lys Asn Ser Val Gly Arg Trp Lys Glu Ala Thr Ile Pro
            20                  25                  30

Gly His Leu Asn Ser Tyr Thr Ile Lys Gly Leu Lys Pro Gly Val Val
                35                  40                  45

Tyr Glu Gly Gln Leu Ile Ser Ile Gln Gln Gly Ser Pro Gly Ile His
    50                  55                  60

Arg Asp
65
```

(2) INFORMATION FOR SEQ ID NO:13:

(i) SEQUENCE CHARACTERISTICS:
        (A) LENGTH: 89 amino acids
        (B) TYPE: amino acid
        (D) TOPOLOGY: linear (ii) MOLECULE TYPE: peptide (xi) SEQUENCE DESCRIPTION: SEQ ID NO:13:

```
Met Arg Gly Ser Asn Ala Pro Gln Pro Ser His Ile Ser Lys Tyr Ile
1               5                   10                  15

Leu Arg Trp Arg Pro Lys Asn Ser Val Gly Arg Trp Lys Glu Ala Thr
            20                  25                  30

Ile Pro Gly His Leu Asn Ser Tyr Thr Ile Lys Gly Leu Lys Pro Gly
                35                  40                  45

Val Val Tyr Glu Gly Gln Leu Ile Ser Ile Gln Gln Tyr Gly His Gln
    50                  55                  60

Glu Val Thr Arg Phe Asp Phe Thr Thr Thr Ser Thr Ser Thr Pro Gly
65              70                  75                      80

Ser Arg Ser His His His His His
                85
```

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: C-terminal (xi) SEQUENCE DESCRIPTION: SEQ ID NO:14:

```
Gly Ser Pro Gly Ile His Arg Asp
1               5
```

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:15:

```
Met Arg Gly Ser
1
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: C-terminal ( x i ) SEQUENCE DESCRIPTION: SEQ ID NO:16:

```
Gly Ser Arg Ser His His His His His His
1               5                   10
```

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:17:

```
Ala Gln Asn Pro Ser
1               5
```

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:18:

```
Glu Glu His Gly Phe
1               5
```

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide (v) FRAGMENT TYPE: N-terminal (xi) SEQUENCE DESCRIPTION: SEQ ID NO:19:

Ala Val Gly Asp Glu
1               5

(2) INFORMATION FOR SEQ ID NO:20:

(i) SEQUENCE CHARACTERISTICS:
        (A) LENGTH: 9 base pairs
        (B) TYPE: nucleic acid
        (C) STRANDEDNESS: single
        (D) TOPOLOGY: circular (ix) FEATURE:
        (A) NAME/KEY: CDS
        (B) LOCATION: 1..9

(ix) FEATURE:
        (A) NAME/KEY: misc_feature
        (B) LOCATION: 1..9
        (D) OTHER INFORMATION: /note= "III-1-C"

(xi) SEQUENCE DESCRIPTION: SEQ ID NO:20:

AAT GCA CCA                                                                 9
Asn Ala Pro
1

(2) INFORMATION FOR SEQ ID NO:21:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO:21:

Asn Ala Pro
1

(2) INFORMATION FOR SEQ ID NO:22:

(i) SEQUENCE CHARACTERISTICS:
        (A) LENGTH: 6 base pairs
        (B) TYPE: nucleic acid
        (C) STRANDEDNESS: single
        (D) TOPOLOGY: circular (ix) FEATURE:
        (A) NAME/KEY: CDS
        (B) LOCATION: 1..6

(xi) SEQUENCE DESCRIPTION: SEQ ID NO:22:

ACA CCT                                                                     6
Thr Pro
1

(2) INFORMATION FOR SEQ ID NO:23:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:23:

Thr Pro
1

( 2 ) INFORMATION FOR SEQ ID NO:24:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: circular ( i x ) FEATURE:
        ( A ) NAME/KEY: CDS
        ( B ) LOCATION: 1..9

( i x ) FEATURE:
        ( A ) NAME/KEY: misc_feature
        ( B ) LOCATION: 1..9
        ( D ) OTHER INFORMATION: /note= "III-1-E"

( x i ) SEQUENCE DESCRIPTION: SEQ ID NO:24:

```
A A T   G C A   C C A                                                     9
A s n   A l a   P r o
  1
```

( 2 ) INFORMATION FOR SEQ ID NO:25:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
A s n   A l a   P r o
  1
```

( 2 ) INFORMATION FOR SEQ ID NO:26:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: circular ( i x ) FEATURE:
        ( A ) NAME/KEY: CDS
        ( B ) LOCATION: 1..6

( x i ) SEQUENCE DESCRIPTION: SEQ ID NO:26:

```
C A G   C A G                                                             6
G l n   G l n
  1
```

( 2 ) INFORMATION FOR SEQ ID NO:27:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
G l n   G l n
  1
```

( 2 ) INFORMATION FOR SEQ ID NO:28:

( i ) SEQUENCE CHARACTERISTICS:
        ( A ) LENGTH: 27 base pairs
        ( B ) TYPE: nucleic acid ( C ) STRANDEDNESS: single
( D ) TOPOLOGY: circular ( i x ) FEATURE:
( A ) NAME/KEY: CDS
( B ) LOCATION: 1..27

( x i ) SEQUENCE DESCRIPTION: SEQ ID NO:28:

```
AAA  TCG  GAT  CTG  GTT  CCG  CGT  GGA  TCC                    27
Lys  Ser  Asp  Leu  Val  Pro  Arg  Gly  Ser
 1                   5
```

( 2 ) INFORMATION FOR SEQ ID NO:29:

( i ) SEQUENCE CHARACTERISTICS:
( A ) LENGTH: 9 amino acids
( B ) TYPE: amino acid
( D ) TOPOLOGY: linear ( i i ) MOLECULE TYPE: protein ( x i ) SEQUENCE DESCRIPTION: SEQ ID NO:29:

```
Lys  Ser  Asp  Leu  Val  Pro  Arg  Gly  Ser
 1                   5
```

( 2 ) INFORMATION FOR SEQ ID NO:30:

( i ) SEQUENCE CHARACTERISTICS:
( A ) LENGTH: 27 base pairs
( B ) TYPE: nucleic acid
( C ) STRANDEDNESS: single
( D ) TOPOLOGY: circular ( i x ) FEATURE:
( A ) NAME/KEY: CDS
( B ) LOCATION: 1..25

( x i ) SEQUENCE DESCRIPTION: SEQ ID NO:30:

```
GGA  TCC  CCG  GGA  ATT  CAT  CGT  GAC  T  GA                  27
Gly  Ser  Pro  Gly  Ile  His  Arg  Asp
 1                   5
```

( 2 ) INFORMATION FOR SEQ ID NO:31:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:31:

```
Gly  Ser  Pro  Gly  Ile  His  Arg  Asp
 1                   5
```

( 2 ) INFORMATION FOR SEQ ID NO:32:

( i ) SEQUENCE CHARACTERISTICS:
( A ) LENGTH: 21 base pairs
( B ) TYPE: nucleic acid
( C ) STRANDEDNESS: single
( D ) TOPOLOGY: circular ( i x ) FEATURE:
( A ) NAME/KEY: CDS
( B ) LOCATION: 1..21

( x i ) SEQUENCE DESCRIPTION: SEQ ID NO:32:

```
ATG  AGA  GGA  TCC  AAT  GCA  CCA                              21
Met  Arg  Gly  Ser  Asn  Ala  Pro
 1                   5
```

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Met  Arg  Gly  Ser  Asn  Ala  Pro
 1                    5
```

( 2 ) INFORMATION FOR SEQ ID NO:34:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: circular ( i x ) FEATURE:
        ( A ) NAME/KEY: CDS
        ( B ) LOCATION: 1..37

( x i ) SEQUENCE DESCRIPTION: SEQ ID NO:34:

```
ACA  CCT  GGA  TCC  AGA  TCT  CAT  CAC  CAT  CAC  CAT  CAC  T  AA    39
Thr  Pro  Gly  Ser  Arg  Ser  His  His  His  His  His  His
 1                    5                         10
```

( 2 ) INFORMATION FOR SEQ ID NO:35:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

```
Thr  Pro  Gly  Ser  Arg  Ser  His  His  His  His  His  His
 1                    5                         10
```

FIBRONECTIN TYPE III POLYPEPTIDES

RELATED APPLICATIONS

This application is a continuation of application Ser. No. 08/340,812, U.S. Pat. No. 5,629,291, filed Nov. 17, 1994 which is a continuation of application Ser. No. 08/021,626, filed Feb. 16, 1993, now abandoned, which is a continuation-in-part of application Ser. No. 07/829,462, U.S. Pat. No. 5,453,489 filed Jan. 31, 1992, the contents of which are incorporated herein by reference.

ACKNOWLEDGEMENT

This invention was made with Government support under Grant No. CA42507, and Cancer Center Support Grant No. CA30199, both awarded by the National Cancer Institute. The Government has certain rights in the invention.

FIBRONECTIN TYPE III POLYPEPTIDES

FIELD OF THE INVENTION

The present invention relates to fibronectin extracellular matrix assembly and compounds involved in extracellular matrix assembly. In particular, the present invention relates to methods of modulating fibronectin extracellular matrix assembly and related biological processes.

BACKGROUND OF THE INVENTION

As a constituent of the extracellular matrix, fibronectin is important for allowing cells to attach to the matrix. Fibronectin influences both the growth and migration of cells. Normal fibroblasts in tissue culture secrete fibronectin and assemble it into a matrix that is essential to their adhesion and growth. While many tumorigenic cells continue to produce fibronectin, they do not assemble the fibronectin into a matrix. This lack of matrix assembly is thought to contribute to the invasive properties of malignant cells. Thus, one important stage in the progression of cancer may be the transition from assembly to non-assembly of the extracellular matrix.

The general structure of fibronectin has been identified. The polypeptide is composed of a number of repeats, of which there are three kinds, type I, type II, and type III. The type I repeat is about 45 amino acids long and makes up the amino-terminal and carboxy-terminal ends of the polypeptide. Two 60 amino acid type II repeats interrupt a row of nine type I repeats at the amino-terminus of fibronectin. Finally, 15 to 17 type III repeats, each about 90 amino acids long, make up the middle of the polypeptide. Altogether, mature, i.e., processed, fibronectin contains nearly 2500 amino acid residues.

Matrix assembly requires the binding of fibronectin to cell surfaces followed by assembly into fibrils, and stabilization of the fibrils by disulfide cross-linking. Several regions within fibronectin are required for the assembly process. The amino terminal 70 kDa region of fibronectin is known to bind to another molecule, the identity of which is unknown. (McKeown-Longo et al. *J. Cell. Biol.* 100 364 (1985), Mosher et al. *Ann. N.Y. Acad. Sci* 614 167 (1991).

The fibronectin molecule may be characterized as containing both heparin-binding regions and gelatin-binding regions. Another region considered to be involved in the fibronectin assembly process is the amino terminal 29 kDa heparin binding domain. Cells have been shown to organize fibronectin fragments into fibrils only when heparin-binding fragments and an RGD-containing cell binding domain were present simultaneously (Woods et al., *Exp. Cell Res.* 177:272–283 (1988)). The importance of the 29 kDa heparin-binding domain has been further underscored by the finding that recombinant fibronectin molecules lacking the 29 kDa region are not incorporated into extracellular matrix (Schwarzbauer, *J. Cell Biol.* 113:1463–1473 (1991)). Moreover, molecules composed only of the 29 kDa region, plus the carboxy-terminal half of fibronectin were efficiently incorporated into the extracellular matrix. In view of the above information, the role of the 29 kDa region appears to mediate the binding of fibronectin to the cell surface.

Another region involved in matrix assembly is the RGD (arginine-glycine-aspartic acid)-containing cell binding domain of fibronectin. Monoclonal antibodies directed to the cell binding domain of fibronectin have been found to inhibit assembly of extracellular matrix (McDonald et al., *J. Biol. Chem.* 262:2957–2967 (1987)). In addition, two-monoclonal antibodies have been described that bind close to, but not directly to, the RGD site. These antibodies block the binding of cells to fibronectin and also block fibronectin matrix assembly (Nagai et al., *J. Cell Biol.* 114:1295–1305 (1991)).

The receptor that binds to the RGD site in fibronectin is, in most cells, the $\alpha_5\beta_1$ integrin (Pierschbacher and Ruoslahti, *Nature* 309:30–33 (1984)). Accordingly, monoclonal antibodies directed against the $\alpha_5$ and $\beta_1$ integrin subunits have also been found to inhibit fibronectin matrix assembly, as well as the binding of fibronectin to matrix assembly sites. Conversely, overexpression of the $\alpha_5\beta_1$ integrin in CHO cells results in increased fibronectin matrix assembly. Taken together, these findings establish the importance of the interaction between fibronectin and the $\alpha_5\beta_1$ integrin during matrix assembly.

A third region of fibronectin has recently been shown to be involved in matrix assembly. A 56 kDa fragment from fibronectin, which contains the 40 kDa gelatin-binding domain, plus the first type III repeat has been found to inhibit the incorporation of exogenous fibronectin into the extracellular matrix (Chernousov et al., *J. Biol. Chem.* 266:10851–10858 (1991)). In addition, monoclonal antibodies that bind within this 56 kDa region were also found to block fibronectin matrix assembly.

Because of its role in the extracellular matrix, fibronectin is important in both normal and pathological tissues. The identification of additional regions of fibronectin involved in the assembly of extracellular matrix will provide additional means to control the matrix assembly process. Such control is useful in many biologically and medically important situations, such as culturing cells and directing tissue regeneration, and ameliorating certain pathological conditions.

SUMMARY OF THE INVENTION

The present invention provides substantially purified polypeptides which contain fibronectin-fibronectin binding sites, also referred to as fibronectin self-assembly sites. A first set of polypeptides derived from the type $III_1$ repeat of fibronectin containing a fibronectin-fibronectin binding site has been used to obtain a second set of polypeptides derived from the C-terminal type I repeats of fibronectin. The second set of polypeptides contains a fibronectin-fibronectin binding site capable of interacting with the first binding site. The type $III_1$-derived polypeptides include a 14 kDa fragment, recombinant versions of the 14 kDa fragment referred to as $III_1$-C, $III_1$-E, and QE-C, and synthetic polypeptides P1 through P4 derived from the 14 kDa fragment. The C-terminal type I derived polypeptides include an 18 kDa fragment, and synthetic polypeptides P11, representing the 11th type I repeat, and P12, representing the 12th type I repeat. The P11 polypeptide in particular binds strongly to the first set of polypeptides. A number of the polypeptides of the present invention inhibit fibronectin-fibronectin binding to some degree, and thereby inhibit the formation of the fibronectin extracellular matrix. This is in contrast to previously identified fibronectin fragments that block fibronectin matrix assembly by blocking fibronectin binding to cells.

In addition, the present invention provides methods of both inhibiting and promoting extracellular matrix formation, and therefore methods of controlling biological processes related to matrix formation. The present invention further provides methods of isolating fibronectin, and promoting cell attachment to surfaces employing the invention polypeptides.

BRIEF DESCRIPTION OF THE FIGURES

FIG. 21 illustrates the reduction of CHO cell migration by the application of the $III_1$-C polypeptide, where

DETAILED DESCRIPTION OF THE INVENTION

Figure 1:
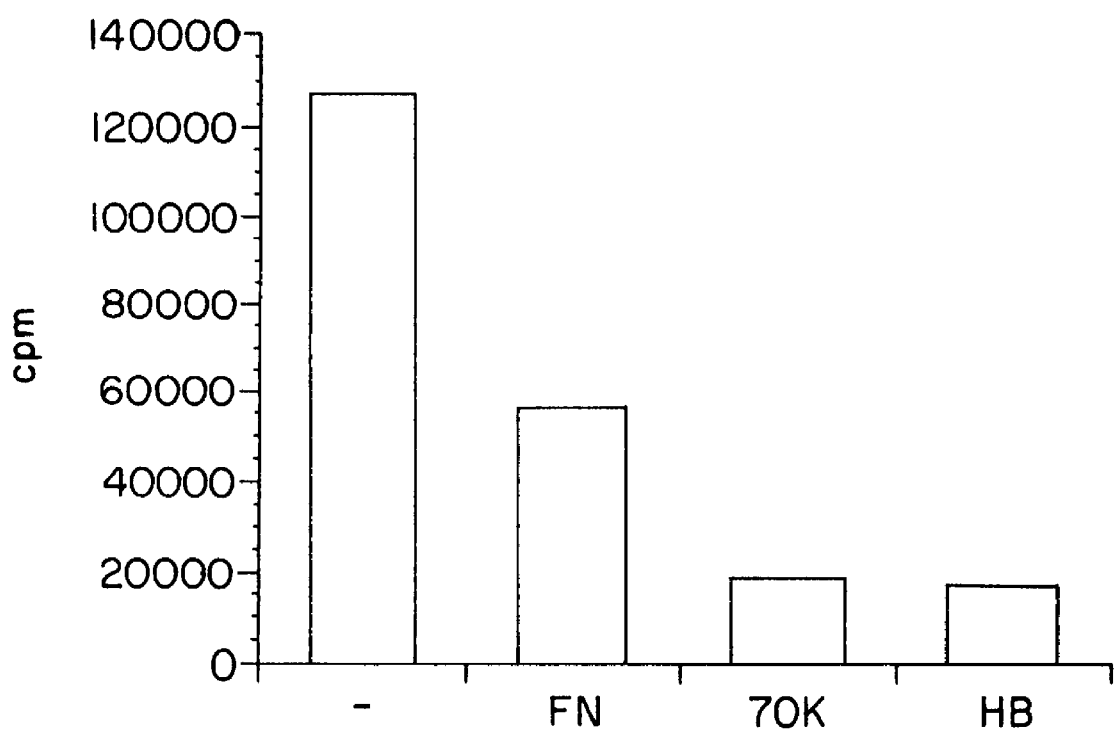
FIG. 1 illustrates the inhibition of fibronectin matrix assembly by fibronectin, 70 kDa fragment, and heparin binding fragments of fibronectin.

As used herein the term "substantially" or "essentially" when referring to the amino acid sequence of a polypeptide refers to sequences having variations in the sequence of amino acids such that at least a portion of the desired activity of the original polypeptide is retained. Such variations include substitutions, additions or deletions of amino acids in a sequence, fragments of the sequences, or multiple copies of the sequence such that at least a portion of the desired activity is retained. In the context of the polypeptides of the present invention, this activity can be protein-protein binding such as binding to fibronectin, inhibition of fibronectin-fibronectin binding, inhibition of matrix formation, promotion of cell attachment, or other activities described in detail in the Examples below.

As used herein the term "polypeptide" refers to fragments isolated from a larger molecule by proteolytic cleavage, as well as polypeptides which are produced recombinantly, polypeptides produced by chemical synthesis, or polypeptides or polypeptide fragments made by other methods. Exemplary polypeptides contemplated by the present invention include those which have substantially the same amino acid sequence as set forth in Sequence ID No. 1 through 7. The term "polypeptide" also refers to "functional fragments", which are sequences containing less than all of the residues set forth in Sequence ID No. 1 to 7 which also retain at least a portion of the functional activity of the parent polypeptide.

The term "polypeptide" also refers to homologous polypeptides from different species, allelic variations within the same species, multimeric forms of the polypeptides or functional fragments of the multimeric forms. For example, the polypeptide P1 is known to aggregate into multimers above certain concentrations, as described in Example VI.

As used herein, the term "cellular system" refers to an in vitro cellular system such as cell cultures as described in the Examples below, and in vivo systems such as specific tissues in mammalian organisms.

As used herein the term "binding molecule" refers to protein or non-protein molecules which bind to the polypeptides of the present inventions. Binding molecules as used herein refers to antibodies, proteins other than the proteins of the present invention, RNA molecules and other molecules which bind to the invention polypeptides. As used herein the term "antibodies" refers to any molecule which has specific immunoreactive activity. Such a molecule may be optionally coupled with another compound such as a targeting agent, carrier, label, toxin, or drug. Although an antibody usually comprises two light and two heavy chains aggregated in a "Y" configuration with or without covalent linkage between them, the term is also meant to include a reactive fragment or fragments such as Fab molecules, Fab proteins or single chain polypeptides having binding affinity for an antigen. "Fab" refers to antigen binding fragments. As used herein the term "Fab molecules" refers to regions of antibody molecules which include the variable portions of the heavy chain and/or light chain and which exhibit binding activity. "Fab protein" includes aggregates of one heavy and one light chain (commonly known as Fab), as well as tetramers which corresponds to the two branch segments of the antibody Y (commonly known as F(ab)$_2$), whether any of the above are covalently or non-covalently aggregated so long as the aggregation is capable of selectively reacting with a particular antigen or antigen family. Also included in the definition of "antibody" are immunoreactive polypeptides which have been recombinantly synthesized, chemically synthesized, recombinantly combined, chemically modified or chemically linked.

The present invention provides substantially purified polypeptides containing fibronectin self-association sites. These polypeptides themselves bind to fibronectin, and are also capable of inhibiting the binding of one fibronectin molecule to another fibronectin molecule.

A first set of fibronectin-binding polypeptides containing a fibronectin-fibronectin binding site is provided. These polypeptides were derived from the first type III (III$_1$) repeat of fibronectin. This set of polypeptides includes a 14 kDa fragment, recombinantly produced versions of the 14 kDa fragment, and synthetic functional fragments of the 14 kDa fragment.

The 14 kDa fragment and exemplary synthetic subfragments have been characterized and sequenced. The 14 kDa fragment was isolated from heparin-binding fragments of fibronectin by screening for fragments having the capacity to inhibit extracellular matrix assembly as described in Example III. This fragment is considered to encompass the first type III repeat unit of fibronectin. The 14 kDa fragment has the following sequence: NAPQPSHISK YILRWRPKNS VGRWKEATIP GHLNSYTIKG LKPGVVYEGQ LISIQQYGHQ EVTRFDFTTT STSTPVTSNT VTGETTPFSP LVATSESVTE ITASSFVVS (Sequence ID No 1).

The 14 kDa fragment is further characterized by being capable of binding to IMR-90 cells, which construct an extensive fibronectin extracellular matrix, and not to HT-1080 cells, which produce no matrix. IMR-90 cells are a human diploid lung fibroblast non-tumorigenic cell line, having the ATCC number CCL-186. HT-1080 cells are a human fibrosarcoma tumorigenic cell line, having the ATCC number CCL-121. The 14 kDa fragment has the further ability to greatly reduce the formation of the fibronectin matrix, by approximately 70 percent in some experiments (see Example IV below). This inhibition of matrix formation is found to be due to the binding of the fragment to the fibronectin molecule, thus competing with fibronectin-fibronectin binding, as described in Example V below, rather than interfering with the binding of fibronectin to the cells, as is demonstrated in Example VII.

Functional fragments of the 14 kDa fragment are also provided. These fragments include four subfragments designated P1 through P4, which represent various overlapping segments of the 14 kDa fragment, as described in Example I. The amino acid sequences of these four functional subfragments are as follows:

NAPQPSHISK YILRWRPKNS VGRWKEATIP G (P1; Sequence ID No. 2);

EATIPGHLNS YTIKGLKPGV VYEGQLISIQ Q (P2; Sequence ID No. 3);

LISIQQYGHQ EVTRFDFTTT STSTPVTSNT V (P3; Sequence ID No. 4);

VTSNTVTGET TPFSPLVATS ESVTEITASS FVVS (P4; Sequence ID No. 5).

A presently preferred polypeptide subfragment for use in the present invention is the polypeptide designated P1. As described in Example IV, and shown in FIG. 7, P1 is highly effective in inhibiting the binding of the 14 kDa fragment to fibronectin (shown in FIG. 7A), and in inhibiting the binding of fibronectin to fibronectin (FIG. 7B). As described in Example VI, P1 reduces the incorporation of fibronectin into the extracellular matrix by 80 percent or more in some experiments.

Recombinant versions of the 14 kDa fragment, herein referred to as the III$_1$-C, III$_1$-E, and QE-C polypeptides are also provided. The production of these recombinant polypeptides is described in Example I. The III$_1$-C and QE-C polypeptides were produced by splicing the same PCR-produced sequence into two different vectors, as described in Example I. The sections of the fibronectin molecule corresponding to the III$_1$-derived synthetic and recombinant polypeptides are shown on FIG. 14. The three recombinant polypeptides contain N-terminal amino acids and C-terminal amino acids which are not found in the original fibronectin sequence, as described in Example I.

The binding affinity of III$_1$-E for fibronectin has been determined by Scatchard analysis, as described in Example XI. The analysis determined that there are both high affinity, low abundance sites, ($K_D$ of about 6×10$^{-8}$M with approximately 1–2 binding sites per fibronectin dimer), and low affinity, high abundance sites ($K_D$ of about 6×10$^{-7}$M, with approximately 10 binding sites per fibronectin dimer) on fibronectin for the III$_1$-E fragment.

Figure 16A:
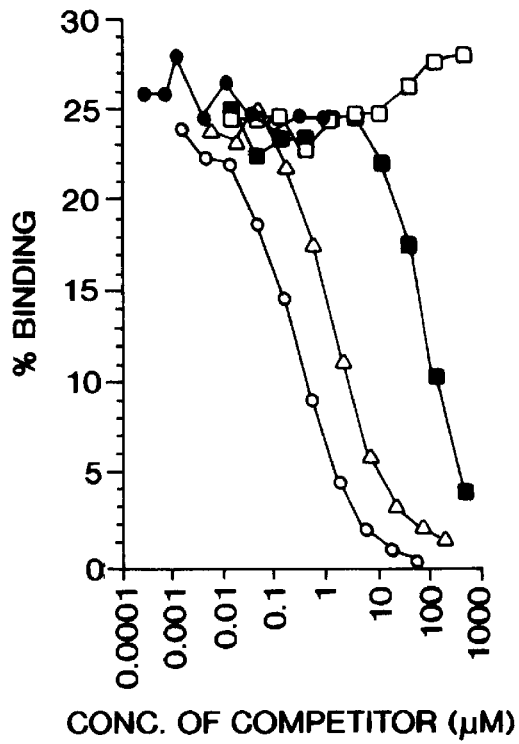
FIG. 16 illustrates the inhibition of $III_1$-E-fibronectin binding (FIG. 16A), and fibronectin-fibronectin binding (FIG. 16B) in the presence of fibronectin, $III_1$-E, P1, P11, and P12.

The III$_1$-derived recombinant polypeptides were shown to have the ability to both inhibit and enhance fibronectin-fibronectin binding and fibronectin matrix assembly. Example X describes the biphasic nature of III$_1$-E inhibition of fibronectin-fibronectin binding, as shown in FIG. 16A, in that III$_1$-E inhibits binding at low concentrations and enhances it at higher concentrations. Example XIII describes the enhancement of fibronectin matrix assembly by the recombinant polypeptides, such as III$_1$-C. Example XII describes the stimulation of in vitro disulfide cross-linkage formation by the recombinant $III_1$ polypeptides, in particular $III_1$-C. In addition, it was shown in Example XIV that CHO cell migration can be slowed by the application of the recombinant polypeptides to the cell culture, indicating that the migration of tumor cells can be inhibited by the polypeptides of the present invention.

A second set of polypeptides derived from the C-terminal type I repeats of fibronectin is also provided. These polypeptides contain a fibronectin-fibronectin binding site which interacts with the first binding site contained in the $III_1$ repeat of fibronectin and represented by the first set of polypeptides. The second set of polypeptides includes an 18 kDa fragment, and synthetic polypeptides representing the eleventh type I repeat, designated P11, and the twelfth type I repeat, designated P12. These polypeptides bind fibronectin and also have the ability to inhibit fibronectin-fibronectin binding by competing for binding sites with the fibronectin molecules.

The 18 kDa fragment was isolated by eluting fragments of digested fibronectin which bound a P1-Sepharose column as described in Example IX. This fragment was found to represent the 12th, 11th, and part of the 10th type I repeat of fibronectin. Synthetic polypeptides representing the 11th and 12th repeats were synthesized. The sequences are as follows: RWSHDNGVNY KIGEKWDRQG ENGQMMSSTS LGNGKGEFKS DPHE (P11; Sequence ID No. 6), and ATSYDDGKTY HVGEQWQKEY LGAISSSTSF GGQRGWRSDN SR (P12, Sequence ID No. 7). Of these synthetic polypeptides, P11 is the preferred embodiment and is found to be the most effective at inhibiting both $III_1$-E-fibronectin binding, and fibronectin-fibronectin binding, as is shown in Example IX.

In another aspect of the present invention, there are provided binding molecules which bind to the polypeptides of the present invention. Such binding molecules can be proteins or non-proteins and include antibodies raised against the polypeptides of the present invention, including antibody-like proteins such as recombinant antibodies, single-chain antibodies, and the like as described above, as well as recombinant protein fragments and RNA sequences that specifically bind the polypeptides. One skilled in the art can readily prepare such binding molecules, without undue experimentation, given the sequence and description of the fibronectin-binding polypeptides provided herein. These various molecules can be provided as compositions for producing a desired biological effect by increasing or decreasing fibronectin matrix formation.

In another aspect of the present invention, a method of inhibiting the ability of fibronectin to participate in extracellular matrix assembly by blocking fibronectin-fibronectin binding is provided. This is accomplished by contacting the cells or tissues to be treated with an effective amount of the polypeptides of the present invention, as described extensively in the Examples below. Blocking fibronectin-fibronectin binding can also be accomplished by contacting the targeted cells or tissue with an effective amount of binding molecules made against the invention polypeptides, for example, antibodies made against the invention polypeptides. Blocking or inhibiting fibronectin-fibronectin binding is accomplished by the binding of the polypeptides or binding molecules with the reciprocal binding site on the fibronectin molecule, thus preventing fibronectin-fibronectin binding.

The ability to inhibit the formation of extracellular matrix is of great benefit in controlling biological processes which are related to extracellular matrix accumulation. For example scar formation is related to the formation of excess extracellular matrix accumulation. Therefore, treatment with the polypeptides and related molecules of the present invention is a method for preventing unwanted scar formation. Therefore, in another aspect of the present invention, a method to prevent scar formation as a result of the healing of a wound is provided, by administering an effective amount of invention polypeptide so as to enhance cell migration into a wound site, while preventing excessive matrix formation, thereby preventing scar formation.

In another aspect of the present invention, the polypeptides of the present invention have also shown the unexpected characteristic of enhancing fibronectin binding to surfaces at higher concentrations of the polypeptides. As described in Example VIII, the polypeptides of the present invention can promote cell attachment to surfaces when the surface is coated with the polypeptide, then incubated with fibronectin under conditions allowing for the binding of fibronectin. Coating a surface such as plastic wells with a polypeptide and fibronectin is shown to promote cell attachment. Therefore, the present invention provides a method of promoting cell attachment to a surface through the use of the invention polypeptides. Since the invention polypeptides bind fibronectin such as plasma fibronectin, they can be used to coat biological and medical materials such as, for example, implants, so that the materials bind fibronectin from biological fluid, and thereby become adhesive to cells, thereby enhancing the biocompatibility of such materials.

The polypeptides of the present invention also have the unexpected property of both reducing fibronectin-fibronectin binding at low concentrations of the polypeptides, while enhancing fibronectin-fibronectin binding at higher concentrations of the polypeptides, as is described in Example VI and shown in FIG. 7. In addition, the $III_1$-C and related recombinant polypeptides are capable of enhancing fibronectin matrix assembly, as shown in Example XIII. Therefore, the present invention provides a method to promote the assembly of extracellular matrix in a cellular system by contacting the system with an effective amount of the polypeptides of the present invention. The recombinant polypeptides $III_1$-C, $III_1$-E and QE-C, and the synthetic polypeptides P1 and P4 are the presently preferred polypeptides used for this method.

In addition, the polypeptides of the present invention are show to stimulate the formation of fibronectin disulfide cross-linking in vitro. This is described in Example XII. Therefore, fibronectin matrix formation is stimulated by inducing fibronectin-fibronectin disulfide cross-linking. Presently preferred polypeptides for stimulating disulfide bonding are P1, P4, $III_1$-C, $III_1$-E, or QE-C.

The promotion of matrix formation can be used to influence associated biological processes. For example, the promotion of the formation of fibronectin extracellular matrix can be used to combat tumor formation. This is a consequence of the effect of certain polypeptides on fibronectin matrix formation and therefore on cell migration, as described above, and as described in particular detail in Example XIV. It has been previously noted that there is a correlation between an increase in fibronectin matrix assembly and a decrease in tumorigenic phenotype in cell cultures. See, for example, Giancotti and Ruoslahti, *Cell* 60, 849 (1990). A decrease in cell migration was found when the polypeptides of the present invention were applied to the C11 CHO cell line, as described in Example XIV. Therefore, a method of reducing tumor cell migration by applying the polypeptides of the present invention is also provided. Presently preferred polypeptides for use in this method are polypeptides P1, P4, $III_1$-C, $III_1$-E, and QE-C.

Those of skill in the art can readily identify suitable modes of administration of the compositions of the present invention including the polypeptides containing binding sites, antibodies to the polypeptides, RNA encoding the polypeptides, and the like, such as, for example, by injection such as intraperitoneal or subcutaneous, local application such topical application to a surface wound, gradual infusion such as by osmotic pump, and the like.

In another aspect of the present invention the polypeptides could target materials to tissues that contain fibronectin. This is accomplished by coupling the polypeptides with a molecule to be targeted to fibronectin-containing tissues or cells, and contacting the tissues or cells with the coupled molecules.

In accordance with still another embodiment of the present invention, a method is provided to isolate fibronectin from a mixture of proteins by subjecting the mixture to an affinity chromatography column or other support containing one or more of the polypeptides of the present invention, then eluting retained fibronectin from the column or support.

Therefore, the present invention provides polypeptides which contain fibronectin-fibronectin binding sites capable of binding to fibronectin and to each other. The isolation and characterization of fibronectin-fibronectin binding sites contained in the polypeptides of the present invention provides the opportunity for the future construction of chimeric fibronectin which can be tailored for specific uses. The use of the binding site-containing polypeptides presently provides a means to both inhibit and enhance formation of the fibronectin matrix by inhibiting or enhancing fibronectin-fibronectin binding. This in turn provides methods of influencing biological processes which are closely linked to fibronectin matrix formation. The invention polypeptides have other uses as well.

The invention will now be described in greater detail by reference to the following non-limiting examples. These examples are intended to illustrate but not limit the invention.

EXAMPLE I

Isolation of 14 kDa fragment and Synthesis of Polypeptides P1 through P4 Materials The materials used in all of the following examples include the following. Alpha-Minimal Essential Medium (α-MEM) was purchased from Gibco Laboratories (Grand Island, N.Y.), Fetal Calf Serum (FCS) from Tissue Culture Biologicals (Tulare, Calif.), and Glutamine Pen-Strep from Irvine Scientific (Santa Ana, Calif.). Immulon 2 Removawell strips were obtained from Dynatech Laboratories (Chantilly, Va.). Iodo-Gen was purchased from Pierce (Rockford, Ill.). CNBr-activated Sepharose, heparin-Sepharose, gelatin-Sepharose, Sepharose CL-4B, S-Sepharose, NAP-25 columns, and the plasmid vector pGEX-2T were obtained from Pharmacia LKB (Piscataway, N. J.). Precast SDS-PAGE gels were purchased from BioRad (Richmond, Calif.) and Novex (San Diego, Calif.). Imobilon nylon transfer membrane was purchased from BioRad Laboratories (Richmond, Calif.). Vent DNA polymerase was purchased from New England Biolabs, Inc. (Beverly, Mass.). Lab-Tek 8-well Chamber Slides were obtained from Nunc (Naperville, Ill.). HPLC columns were purchased from Vydac (Hesperia, Calif.). Collagen type I was obtained from Collaborative Research (Bedford, Mass.). All other reagents were acquired from Sigma (St. Louis, Mo.). Human fibronectin is commercially available, and was obtained from the Blood Transfusion Service of the Finnish Red Cross in Helsinki.

IMR-90, ATCC number CCL-186, a human diploid lung non-tumorigenic fibroblast cell line, and HT-1080 cells, ATCC number CCL-121, a human fibrosarcoma tumorigenic cell line, are both commercially available. The two cell lines were cultured in α-MEM supplemented with 10% heat-inactivated FCS and Glutamine Pen-Strep. IMR-90 cells used for experiments were between passage number 11 and 20; cells in later passages were not used.

Isolation of fibronectin fragments

To separate heparin-binding fragments from gelatin-binding fragments, fibronectin obtained from the Blood Transfusion Service of the Finnish Red Cross in Helsinki was digested with α-chymotrypsin (0.1% by weight, TLCK treated) for 4 hours at 25° C. The digestion was stopped by adding phenylmethylsulphonyl fluoride (20 μg/ml final concentration). The preparation was passed over a gelatin-Sepharose column according to Engvall and Ruoslahti, *Int. J. Cancer* 20, 1 (1977). After washing the gelatin-Sepharose column with phosphate-buffered saline (PBS), gelatin-bound material was eluted with 8M urea, 50 mM Tris-HCl, pH 7.5, followed by extensive dialysis against distilled water and lyophilization. The material that bound gelatin-Sepharose consisted primarily (over 98%) of fragments of 40 kDa and 45 kDa size. The 40 kDa and 45 kDa fragments do not contain the $III_1$ region and are useful as negative controls in experiments characterizing polypeptides containing binding sites.

The flow-through from the gelatin-Sepharose column was collected and passed over a heparin-Sepharose column. The heparin-Sepharose column was washed with PBS, then heparin-bound fibronectin fragments were eluted with 1M NaCl, 50 mM Tris-HCl, pH 7.5, then dialyzed against distilled water and lyophilized.

The 14 kDa fragment was purified from heparin-binding fragments by reverse phase HPLC on a C-4 column. After applying heparin-binding fragments to the HPLC column in 0.06% trifluoroacetic acid, the column was eluted with a linear gradient of 0 to 60% acetonitrile in 0.06% trifluoroacetic acid. The 14 kDa fragment was eluted in the 45% acetonitrile fractions.

The 14 kDa fragment was sequenced at the Protein Chemistry Laboratory at the La Jolla Cancer Research Foundation, La Jolla, Calif. The sequence of the 14 kDa fragment is NAPQPSHISK YILRWRPKNS VGR-WKEATIP GHLNSYTIKG LKPGVVYEGQ LISIQQYGHQ EVTRFDTTT STSTPVTSNT VTGETTPFSP LVATSESVTE ITASSFVVS (Sequence ID No. 1).

The amino terminal 70 kDa fragment, known to inhibit fibronectin matrix assembly, was also produced from the heparin-binding fibronectin as previously described by McKeown-Longo and Mosher, *J. Cell Biol.* 100:364–374 (1985).

In addition, fibronectin was digested with cathepsin-D as described by McKeown-Longo et al., *J. Cell Biol.* 100, 364 (1985). To remove fragments containing the gelatin-binding domain, the digested fibronectin was applied to a gelatin-Sepharose column according to Engvall and Ruoslahti (1977), supra. The unbound fraction from the gelatin-Sepharose was fractionated further on peptide columns as described in Morla and Ruoslahti, *J. Cell. Biol.* 118, 421 (1992).

Amino-terminal sequence analysis of isolated fibronectin fragments was done by transferring the proteins from a gel onto an Imobilon nylon membrane. The bands of interest were cut out of the membrane and sequenced at the microsequencing facility at the Research Institute of Scripps Clinic (La Jolla, Calif).

Synthesis of polypeptides P1 to P4

Polypeptides representing various regions of the above-described 14 kDa fragment of fibronectin were synthesized at the Protein Chemistry Laboratory at the La Jolla Cancer Research Foundation. All polypeptides used in experiments were purified by reverse phase HPLC. Polypeptide P1 (Sequence ID No. 2) having the sequence NAPQPSHISK YILRWRPKNS VGRWKEATIP G represents the region from amino acids 600 to 630 of fibronectin; polypeptide P2 (Sequence ID No. 3) having the sequence EATIPGHLNS YTIKGLKPGV VYEGQLISIQ Q represents the region from amino acids 625 to 655; polypeptide P3 (Sequence ID No. 4) having the sequence LISIQQYGHQE VTRFDFTTT STSTPVTSNT V represents the region from amino acids 650 to 680; and polypeptide P4 (Sequence ID No. 5) having the sequence VTSNTVTGET TPFSPLVATS ESVTEITASS FVVS represents the region from amino acids 675 to 708 of the mature fibronectin protein according to the numbering method of Kornblihtt et al., *EMBO J.* 4:1755–1759 (1985).

Production of Recombinant Proteins from the First Type III Repeat of Fibronectin (Proteins III$_1$-C, III$_1$-E, and OE-C)

Recombinant proteins representing two different regions of the first type III repeat of fibronectin (see FIG. 14) were produced by PCR cloning of the region in the sequence of human fibronectin spanning residues 600 to 655 (Kornblihtt et al., (1985), supra), for the III$_1$-E protein, and the region spanning residues 600–674 for the III$_1$-C and QE-C proteins. These areas of fibronectin were cloned from a human placental cDNA library previously made using methods well known in the art, using the following PCR primers for the III$_1$-E protein:

5'-primer, 5'-CCGGATCCAATGCACCACAGC CATCTC-3'(Sequence ID No. 8),

3'-primer, 5'-CCGGATCCCTGCTGGATGC TGATGAGC-3' (Sequence ID No. 9).

The following primers were used for the III$_1$-C and QE-C proteins:

5'-primer, 5'-CCGGATCCAATGCACCAC AGCCATCTC-3'(Sequence ID No. 8), (the same primer as used for III$_1$-E);

3'-primer, 5'-CCGGATCCAGGTGTGCTGG TGCTGGTGG-3' (Sequence ID No. 10).

These primers were designed with Bam HI sites flanking the fibronectin-coding sequences to enable splicing of the fibronectin sequence in-frame either with the glutathione-S-transferase coding sequence in the vector pGEX-2T (for III$_1$-E and III$_1$-C, see FIG. 12A), or with the coding sequence in the pQE-12 vector (for QE-C, see FIG. 12B). pGEX-2T was obtained from Pharmacia LKB Biotechnology, Inc., Piscataway, N.J., and pQE-12 was obtained from Qiagen Inc., Chatsworth, Calif.

Figure 12A:
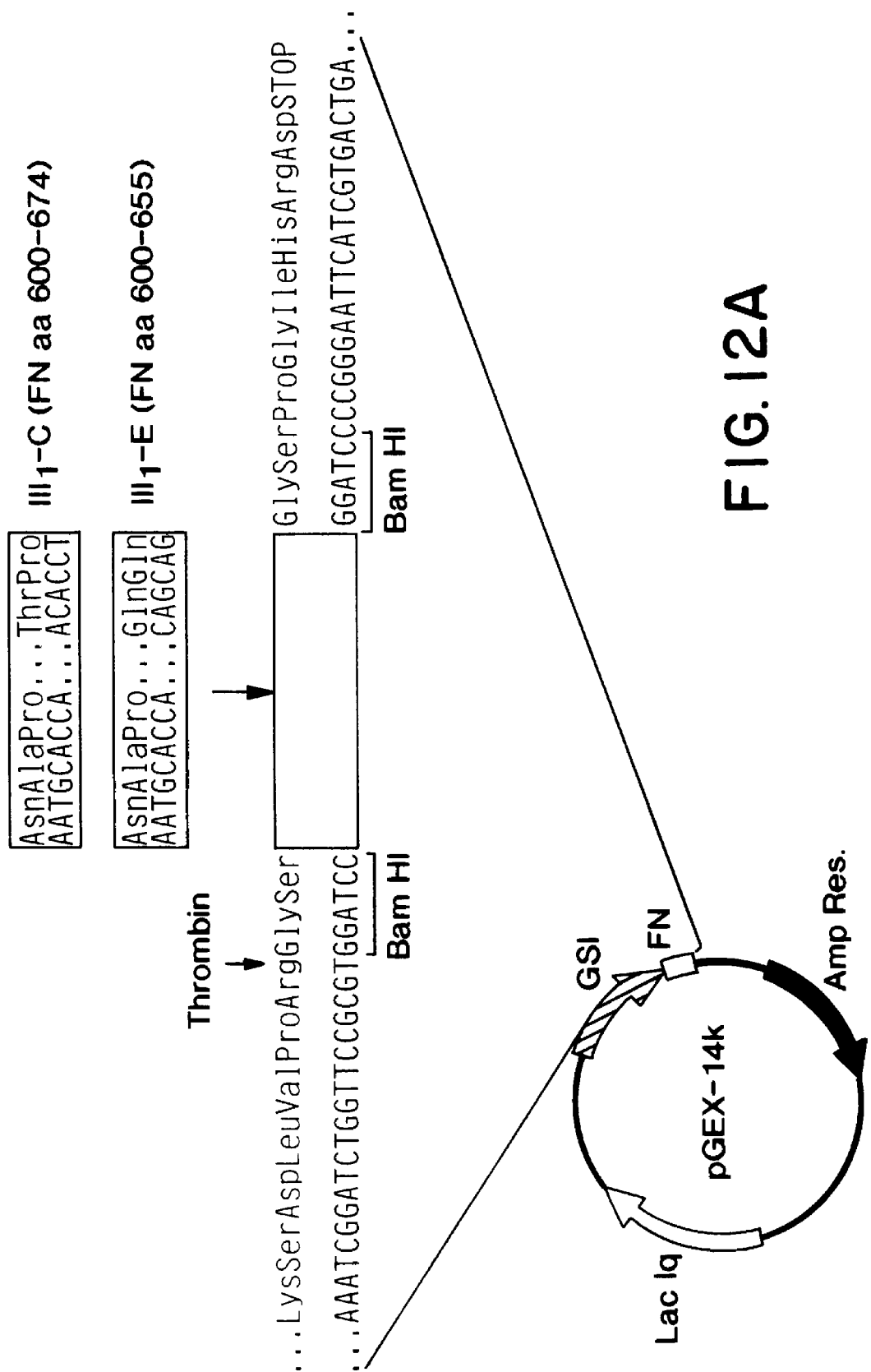
FIG. 12A illustrates the insertion of nucleotide sequences encoding amino acid fragments of human fibronectin into plasmid pGEX-2T (SEQUENCE ID NO.20–31).
Figure 12B:
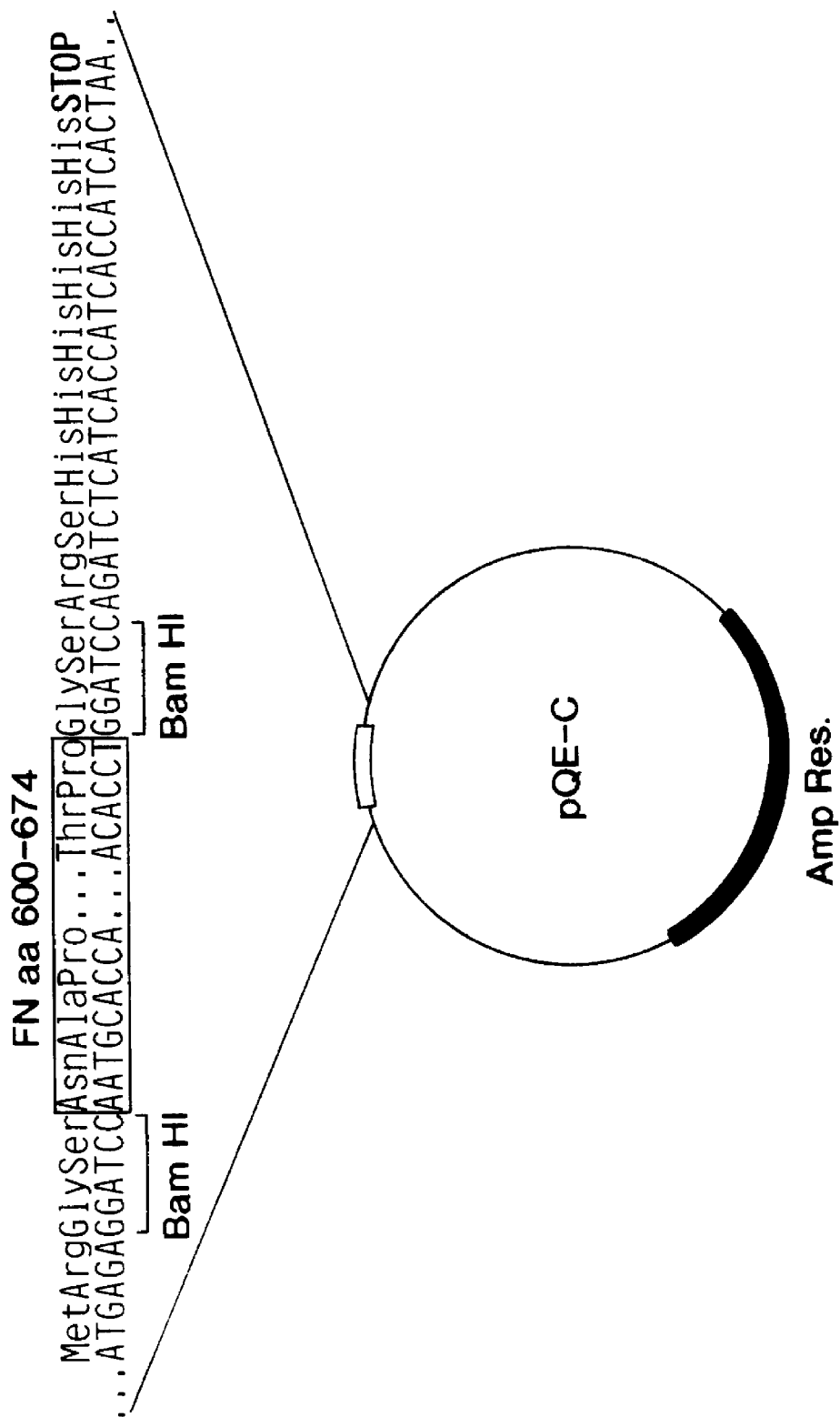
FIG. 12B illustrates the insertion of nucleotide sequences encoding amino acid fragments of human fibronectin into plasmid pQE-12 (SEQUENCE ID NOS.32–35).
Figure 14:
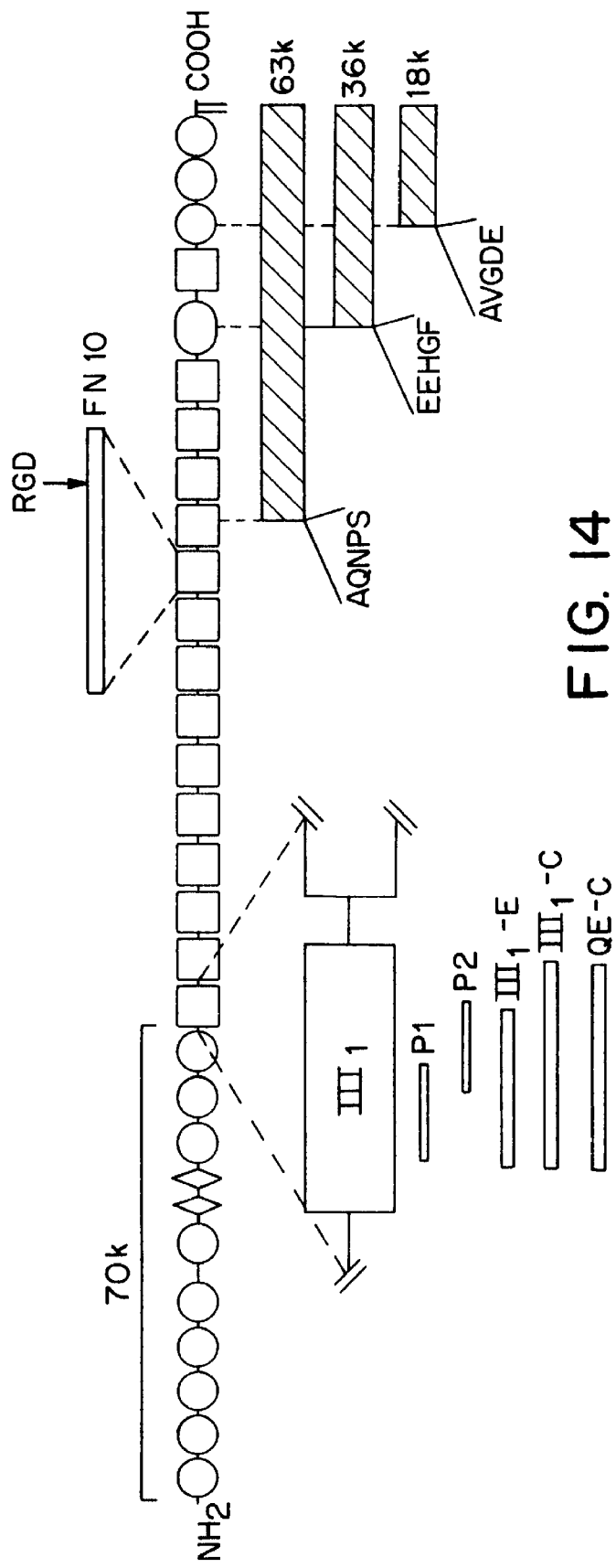
FIG. 14 illustrates a diagram of fibronectin showing the locations of the polypeptides P1 and P2, recombinant polypeptides $III_1$-C, $III_1$-E, and QE-C of the 14 kDa fragment, the amino-terminal 70 kDa fragment, the cell-binding RGD tripeptide, and the regions represented by the 63 kDa fragment containing SEQUENCE. ID. NO. 17, 36 kDa fragment containing SEQUENCE. ID. NO. 18, and 18 kDa fragment containing SEQUENCE. ID. NO. 19.

The PCR reactions were performed using Vent DNA polymerase according to the manufacturer's recommendations, and with the following temperatures and times: 94° C., 1 min; 50° C., 2 min., and 74° C., 2 min., for 30 cycles. The PCR products were purified on agarose gel, digested with Bam HI, purified again on an agarose gel, then ligated into Bam HI-digested and phosphatase-treated pGEX-2T and pQE-12 as shown in FIGS. 12A and B, respectively. XL-1 blue bacteria (Stratagene, La Jolla, Calif.) were transformed with the pGEX-2T plasmid, and M15pREP4 bacteria (Qiagen Inc., Chatsworth, Calif) were transformed with the pQE-12 plasmid, and clones with the appropriate expression products were isolated. When the XL-1 cells were transformed with the pGEX-2T plasmid, the products were designated as III$_1$-C (Sequence ID NO.11)and III$_1$-E(Sequence ID NO.12). When the M15pREP4 cells were transformed with the pQE-12 plasmid, the product was called QE-C. The positions of these polypeptides are illustrated in FIG. 14.

For III$_1$-C and III$_1$-E, a clone with the appropriate expression product was isolated, and synthesis of the proteins was induced by growing the cultures in L-broth plus 50 μg/ml ampicillin, 0.01 mM IPTG for 18 hours at 37° C. with agitation. Cells were collected and lysed, and the glutathione-S-transferase-protein expression products were purified by affinity chromatography on glutathione-agarose as described in Gearing et al., *Bio/Technology* 7, 1157 (1989). The III$_1$-C or III$_1$-E protein was cleaved away from its fusion partner by thrombin digestion according to Smith et al., *Gene* 67, 31 (1988), at the site shown in FIG. 12A. The reaction was carried out in 50 mM Tris-HCl, pH 7.5, 150 mM NaCl, 2.5 mM CaCl$_2$ at 37° C. for 12 hours. The digest was applied to an S-Sepharose column and the III$_1$-C or III$_1$-E protein was purified from digestion products by elution with an NaCl gradient of 0 to 0.4M NaCl in 20 mM Tris-HCL, pH 6.8. The final protein preparations were greater than 95% pure as judged by SDS-PAGE and staining with Coomassie blue. The resulting proteins contain 2 amino acids at the amino terminus (Gly-Ser) and 8 amino acids at the carboxy terminus (Gly-Ser-Pro-Gly-Ile-His-Arg-Asp) (Sequence ID No. 14) which are not normally found in fibronectin.

For the QE-C protein, a clone with the appropriate expression product was isolated, and synthesis of the protein was induced by growing the culture in L-broth plus 50 μg/ml ampicillin, 50 μg/ml kanamycin, 2 mM IPTG for 5 hours at 37° C. with agitation. The protein was prepared according to the manufacturer's recommendations. Briefly, cells were collected and lysed in 6M guanidine HCl, 0.1M NaH$_2$PO$_4$, 0.01M Tris, pH 8.0, and the QE-C protein was purified by affinity chromatography on a Nickel NTA-agarose column (Qiagen Inc., Chatsworth, Calif ). The column was washed with 8M urea, 0.1M NaH$_2$PO$_4$, 0.01M Tris, pH 8.0, and the purified QE-C protein was then removed from the column with 8M urea, 0.1M NaH$_2$PO$_4$, 0.01M Tris, pH 5.9. The purified protein was dialyzed against phosphate-buffered saline to remove the urea buffer. The final QE-C protein preparation was greater than 95% pure as judged by SDS-PAGE and staining with Coomassie blue. The resulting protein contains 4 amino acids at the amino terminus (Met-Arg-Gly-Ser) (Sequence ID No. 15) and 10 amino acids at the carboxy terminus (Gly-Ser-Arg-Ser-His-His-His-His-His-His) (Sequence ID No. 16) which are not normally found in fibronectin.

Iodination of Proteins

Proteins (3–100 μg of protein in 0.1 ml, 50 mM KPO$_4$, pH 7.5) were iodinated by using Iodo-Gen as described in Fraker et al., *Biochem. Biophys. Res. Commun.* 80, 849 (1978). Typical values for specific activity were approximately $10^9$ μCi/mmole for fibronectin, $5 \times 10^8$ μCi/mmole for the 70 kDa fragment, $5 \times 10^8$ μCi/mmole for the isolated 14 kDa fragment and the recombinant polypeptides, and 0.5 μCi/pg for heparin-binding fragments.

EXAMPLE II

ASSAYS

Matrix Assays

Matrix assembly assays were performed by using $^{125}$I-fibronectin, essentially as described previously (McKeown-Longo and Mosher, J. Cell Biol. 97:466–472 (1983); McKeown-Longo and Mosher (1985), supra).

Prior to labeling, IMR cells were grown to confluence in 96-well dishes in α-MEM +10% FCS (fetal calf serum). Cells were labeled in α-MEM +10% fibronectin-deficient FCS plus 5 μCi/ml of $^{125}$I-fibronectin. Fibronectin-deficient FCS was prepared by passing FCS over a gelatin-Sepharose column to remove fibronectin (Engvall and Ruoslahti, *Int. J. Cancer* 20:1–5 (1977)). The concentration of unlabeled fibronectin in α-MEM+10% fibronectin-deficient FCS was approximately 0.2 μg/ml as determined by ELISA using anti-bovine fibronectin antibodies. Where indicated, cells were labeled in the presence of excess non-radioactive competitor proteins such as fibronectin, the 70 kDa fragment, or polypeptides P1 to P4. Cells that were labeled for 1 hour were washed four times with ice-cold PBS, then lysed in 1N NaOH and cell-bound radioactivity was measured in the NaOH soluble fraction. Cells that were labeled with $^{125}$I-heparin-binding fragments were also washed with PBS, then cells were solubilized with SDS-PAGE sample buffer (2% SDS, 67 mM Tris-HCl, pH 6.8, 10% glycerol, 0.03% bromophenol blue) and proteins were separated on BioRad 4–20% Ready Gels, followed by autoradiography. Cells that were labeled with $^{125}$I-fibronectin for 24 hours were washed as described above, then either lysed directly in 4% SDS, 25 mM Tris-HCl, pH 7.5, for a measure of total $^{125}$I-fibronectin, or proteins were separated into 1% deoxycholate soluble and insoluble pools (pools I and II) as described by McKeown-Longo and Mosher (1985), supra. The data presented in FIGS. 4 and 9 (described in greater detail below) depict only specific $^{125}$I-fibronectin binding. Specific binding was defined as that amount of binding which was competed by 2 μM unlabeled fibronectin, and was typically 60–70% of the total $^{125}$I-fibronectin binding.

Protein-protein binding assays

Protein-protein binding assays were performed on Immulon 2, Removawell strips. Proteins were coated onto wells in 100 mM Na$_2$CO$_3$, pH 9.5, in a moist chamber at 4° C. over night. Fibronectin was coated at a concentration of approximately 4 μg/ml. The wells were washed three times with PBS followed by blocking with 0.2% bovine serum albumin in PBS (0.2% BSA) at 37° C. for 1 hour. Radiolabeled proteins were added to the wells in 0.2% BSA at 5 μCi/ml. Proteins were allowed to bind for 24 hours at 37° C., then the wells were washed four times with 0.2% BSA, the wells were removed and the bound $^{125}$I radioisotope was measured.

All of the data represent specific binding, which is defined as binding to fibronectin minus binding to control wells coated with only 2% BSA. The specific binding is typically 75 to 80% of total binding. Binding data were analyzed by using the program LIGAND according to Munson et al., *Anal. Biochem.* 107, 220 (1980).

Affinity chromatography

Polypeptides were coupled to CNBr-activated Sepharose CL-4B according to the manufacturer's recommendations. The concentration of polypeptide was typically 8–10 mg polypeptide/ml of resin. Fibronectin fragments or polypeptides were applied to affinity columns and the flow through fractions were collected.

For affinity chromatography relating to the 14 kDa fragment, and polypeptides P1 through P4, three ml of human plasma was passed over one ml columns of the polypeptides or gelatin-Sepharose as a positive control, or plain Sepharose as a negative control. The flow-through fractions were collected and the columns were washed with 20 column volumes of PBS+5 mM EDTA (PBS/EDTA), followed by 3 column volumes of 0.2M NaCl in PBS/EDTA. Bound proteins were then eluted with 2 volumes of 8M urea in PBS/EDTA, the eluates were collected in two, 1-volume fractions. Equal volumes of each fraction were analyzed by SDS-PAGE on Novex 4–12% Tris-Glycine gels; proteins were visualized by staining with Coomassie blue. The 0.2M NaCl in PBS/EDTA washes contained no significant amounts of protein and are therefore not shown in FIG. 8.

For affinity chromatography as used in Example IX, the columns were washed with 10 volumes of PBS. The bound proteins were eluted with 5 column volumes of 8M urea in PBS. The amount of protein eluted from the column was quantitated by measuring the $A_{280}$ of the solutions.

Reduction and Alkylation of Proteins

Reduction and alkylation of proteins eluted from the column was carried out at a concentration of approximately 1.2 mg/ml solution in 8M urea in PBS. The reduction was performed by adding DTT to a final concentration of 30 mM and incubating the sample at 50° C. for 1.5 hours. The sample was cooled at room temperature, and iodoacetamide was added to a final concentration of 60 mM, and the solution was incubated in the dark at room temperature for 30 minutes. The protein was separated from DTT and iodoacetamide by gel filtration over a NAP-25 column.

In Vitro Cross-linking Assay

In vitro cross-linking assays were performed by adding various concentrations of either QE-C or FN 10 proteins to solutions of 5 μCi/ml $^{125}$I-fibronectin in 2% bovine serum albumin in PBS. The FN 10 protein is a negative control protein produced in the pGEX-2T system, which encompasses the 10th type III repeat of fibronectin, and has no effect in fibronectin-fibronectin binding assays. The solutions were incubated at 37° C. for 20 hours, then samples were collected in SDS-PAGE sample buffer either with or without 1% 2-mercaptoethanol, in order to analyze the $^{125}$I-fibronectin both under reducing and non-reducing conditions. After SDS-PAGE, the gels were dried and exposed to x-ray film to visualize the fibronectin bands. The fibronectin dimer migrates as a band of approximately 450,000 Daltons on a non-reduced gel. On a reduced gel fibronectin runs as a monomer at approximately 250,000 Daltons. Fibronectin from the matrix is disulfide cross-linked into high molecular weight (HMW) aggregates that typically run above 1,000,000 Daltons on a non-reducing gel, and these HMW aggregates run at the same location as monomeric fibronectin on a reducing gel. The extend of in vitro disulfide cross-linking was determined by quantitating the amount of $^{125}$I-fibronectin migrating as HMW aggregates vs. the total amount added to the lane.

Migration Assay (or "Wound" Assay)

Migration was tested by using Chinese Hamster Ovary (CHO) cells in an in vitro "woundings" assay as described previously (Giancotti and Ruoslahti, *Cell* 60,849(1990)). CHO cells are commercially available and have ATCC number CRL 9096. A3 is an overexpressor of the α$_5$β$_1$ integrin created by cDNA transfection as described in the article cited above. C11 is a control-transfected line expressing only the endogenous CHO α$_5$β$_1$. As described in Example XIV below, cells were grown in the absence or presence of 50 μM III$_1$-C for 48 hours, then the culture was "wounded" by removing cells from the plastic dish by scraping the dish with a plastic pipette tip. The migration of the cells into the "wound" path was monitored by photography at various times.

EXAMPLE III

Identification of Fibronectin Fragments containing a First Binding Site

To identify fibronectin fragments containing binding sites that may be important for matrix assembly, fibronectin was digested with chymotrypsin and the preparation was separated into heparin binding and gelatin binding fragments. The fragment preparations were then tested for their ability to inhibit fibronectin matrix assembly by using $^{125}$I-fibronectin and IMR-90 cells, as described by McKeown-Longo and Mosher (1985), supra, and Example II. Among the chymotryptic fragments, the heparin-binding fragments inhibited matrix assembly (FIG. 1), whereas, the gelatin binding fragments had little effect.

The experiments summarized in FIG. 1 were carried out as follows. Confluent monolayers of IMR-90 cells were incubated for 24 hours at 37° C. with $^{125}$I-fibronectin in the presence or absence of unlabeled fibronectin (250 μg/ml), 70 kDa (70 μg/ml), or heparin-binding fragments (1 mg/ml). Cells were washed with PBS, then extracted into deoxycholate soluble and insoluble pools as described above in Example II. The columns represent the amount of $^{125}$I-fibronectin extracted in the deoxycholate insoluble pool. All values are averages of duplicate determinations. Cells were incubated with either no competitor (-), or fibronectin (FN), 70 kDa (70K), or heparin-binding fragments (HB) as competitors of $^{125}$I-fibronectin.

To determine which fragments in the heparin-binding fragment preparation were responsible for inhibiting matrix assembly, $^{125}$I-labeled heparin-binding fragments were incubated with cell monolayers. The fragments that bound to the cells were extracted and analyzed on SDS-PAGE.

Figure 2:
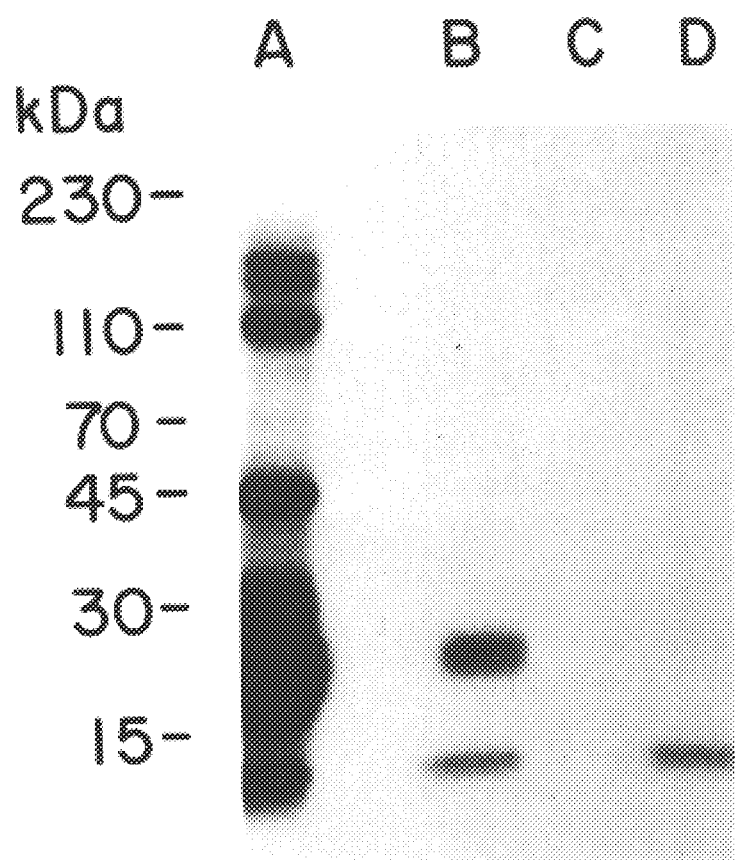
FIG. 2 illustrates the binding of 29 kDa and 14 kDa fragments to IMR-90 cells.

IMR-90 cells were incubated for one hour at 37° C. with $^{125}$I-labeled heparin-binding fragments (2 μCi/ml) in the presence or absence of unlabelled heparin-binding fragments (250 μg/ml), or 70 kDa (1 μM). Cells were then washed with PBS and harvested for analysis by SDS-PAGE as described above. Lane A of FIG. 2 shows a sample of the $^{125}$I-labeled heparin-binding fragment starting material; lane B of FIG. 2 shows fragments that bound in the absence of competition; lane C of FIG. 2 shows fragments bound in the presence of unlabeled heparin-binding fragments; lane D of FIG. 2 shows fragments bound in the presence of unlabeled 70 kDa. The positions of molecular mass standards are indicated to the left of the gel.

Although the heparin-binding fragment preparation contains many polypeptides, ranging from 12 to 200 kDa, only two of these fragments, a 29 kDa fragment and 14 kDa fragment, bound to IMR-90 cells (FIG. 2, lane B). The binding of both fragments was shown to be specific by competition with excess unlabeled heparin-binding fragments (FIG. 2, lanes B and C). Since 29 kDa is the size of the amino terminal heparin binding domain, it was possible that the 29 kDa fragment observed binding to cells in this experiment represented that amino terminal fragment. To test this, cells were incubated with $^{125}$I-labeled heparin-binding fragments in the presence of excess unlabeled amino terminal 70 kDa fragment. The unlabeled 70 kDa fragment competed for the 29 kDa heparin-binding fragment, indicating that this fragment did represent the amino terminal heparin binding domain (FIG. 2, lane D). Interestingly, the 70 kDa fragment did not compete for the 14 kDa heparin-binding fragment (FIG. 2, lane D), suggesting that the 14 kDa region is not represented in the 70 kDa fragment. Thus, the 29 kDa fragment represents the amino terminal heparin binding region, while the 14 kDa fragment apparently lies somewhere outside the amino terminal 70 kDa region.

The 29 kDa amino terminal fragment has been shown to inhibit matrix assembly. See, for example, McKeown-Longo and Mosher (1985), supra; McDonald et al., *J. Biol. Chem.* 262:2957–2967 (1987); Quade and McDonald, *J. Biol. Chem.* 263:19602–19609 (1988)]. It was not clear, therefore, whether the inhibition of matrix assembly caused by heparin-binding fragments was due solely to the 29 kDa fragment, or whether the 14 kDa fragment shared such activity.

Figure 3A:
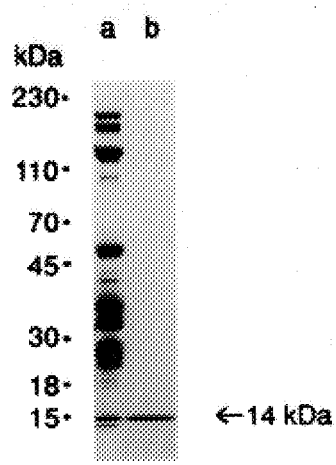
FIG. 3A illustrates the purification of the 14 kDa fibronectin fragment and FIG. 3B illustrates the location of the 14 kDa fragment (SEQUENCE ID NO.1) on the fibronectin molecule.
Figure 3B:
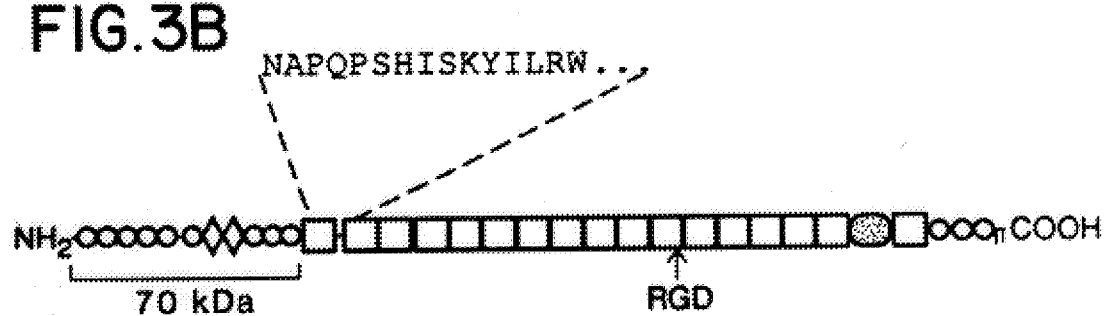

To test this, the 14 kDa fragment was purified to homogeneity by using reverse phase HPLC (FIG. 3A, lane b). Panel A of FIG. 3 shows SDS-PAGE analysis of the heparin-binding fragment starting material (lane a), and the purified 14 kDa preparation (lane b). The gel was stained with coomassie blue. The positions of molecular mass standards are indicated to the left of the gel. The position of the 14 kDa fragment is indicated to the right of the gel. Panel B of FIG. 3 shows a diagram of fibronectin, outlining the locations of the 14 kDa fragment and the various other fragments relevant to the present invention. The three repeating units of fibronectin are depicted as follows; type I repeats, circles; type II repeats, diamonds; type III repeats, squares. The oval represents the CS1 region. The amino terminal sequence of the 14 kDa fragment is shown with dashed lines extending to the location on the diagram representing the area covered by the 14 kDa fragment.

The amino terminal sequence of the 14 kDa fragment (shown in Sequence ID No 1) corresponds to a region just past the beginning of the first fibronectin type III repeat (see FIG. 3B), starting at amino acid residue 600 of the mature protein (according to the numbering of Kornblihtt et al. (1985), supra). Judging from the size of the fragment, it is likely to encompass a sequence that extends partially into the second type III repeat.

EXAMPLE IV

Functional activities of 14 kDa fragment

Binding of the 14 kDa fragment to cells was tested by using IMR-90 cells, which construct an extensive fibronectin matrix, and HT-1080 cells, which produce no matrix, according to the procedure described in Example II. Cells were incubated with purified $^{125}$I-14 kDa in the presence or absence of unlabeled heparin-binding fragments or purified 14 kDa fragment. Approximately 50–60% of the $^{125}$I-14 kDa fragment that bound to IMR-90 cells was competed by unlabeled heparin-binding fragments or 14 kDa fragment. However binding to HT-1080 cells was only at the level of non-specific binding to IMR-90 cells, and none of the $^{125}$I-14 kDa that bound to HT-1080 cells was competed by unlabeled heparin-binding fragments. These data indicate that the 14 kDa fragment binds specifically to IMR-90 cells but not to HT-1080 cells.

The purified 14 kDa fragment was tested for its ability to inhibit matrix assembly. IMR-90 cells were incubated with $^{125}$I-fibronectin in various concentrations of excess unlabeled fibronectin 70 kDa fragment or 14 kDa fragment. Cells were labeled for either 1 hour to assay for fibronectin binding to cell surfaces, or 24 hours to assay for fibronectin incorporation into the extracellular matrix.

With reference to FIG. 4, confluent monolayers of IMR-90 cells were labeled with $^{125}$I-fibronectin in the presence of various concentrations of unlabeled fibronectin (■),70 kDa (●), or 14 kDa (▲). In panel A, cells were labeled for one hour, washed, and the total radioactivity bound was measured. In panel B, cells were labeled for 24 hours and the amount of $^{125}$I-fibronectin in the deoxycholate insoluble pool was measured. Each data point is the average of duplicate determinations.

Figure 4B:
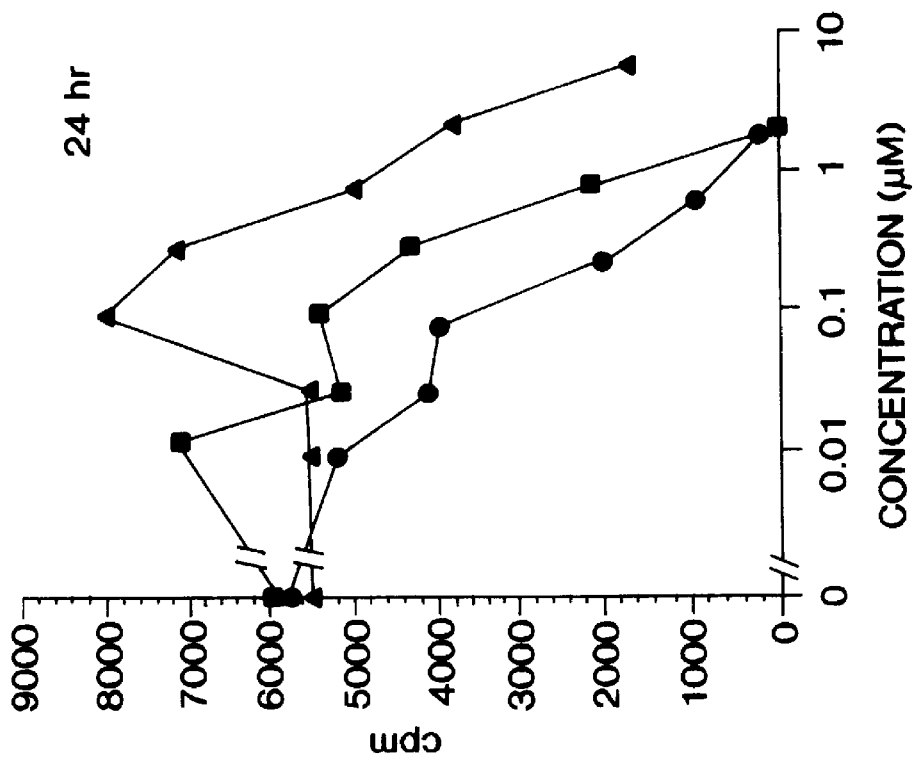
FIG. 4 illustrates the inhibition of fibronectin matrix assembly on IMR-90 cell monolayers by the 14 kDa fragment, the 70 kDa fragment, and fibronectin, after one hour (FIG. 4A), or after 24 hours (FIG. 4B).
Figure 4A:
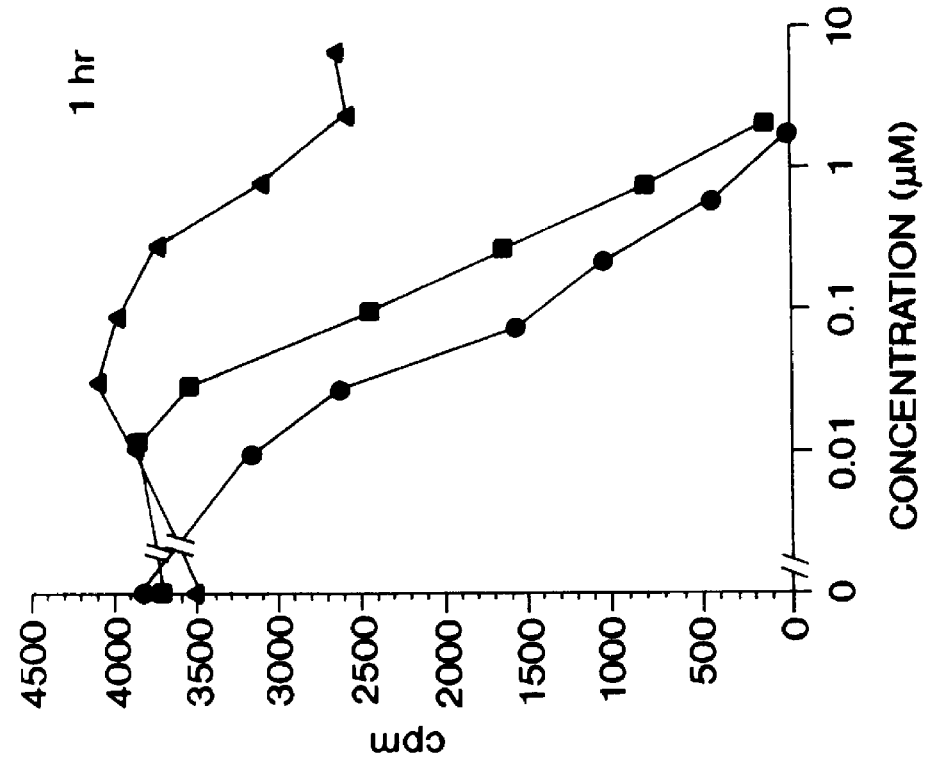

Both fibronectin and the 70 kDa fragment completely inhibited the binding of $^{125}$I-fibronectin to cells, but the 14 kDa fragment only partially reduced the amount of $^{125}$I-fibronectin bound to cells (FIG. 4A). The 14 kDa fragment had a much more pronounced effect on the amount of fibronectin incorporated into the extracellular matrix after 24 hours of incubation with $^{125}$I-fibronectin. As shown in FIG. 4B, the 14 kDa fragment inhibited fibronectin matrix assembly by approximately 70% (at 5 μMr the highest concentration tested). The IC$_{50}$ of the 14 kDa fragment was between 1–2 μM, which was 5–10 fold higher than that of fibronectin or the 70 kDa fragment. Thus, the purified 14 kDa fragment inhibited fibronectin matrix assembly in this assay, and the inhibitory effect seen with heparin-binding fragments was likely due to a combination of the effects of both the 29 kDa and the 14 kDa fragments.

EXAMPLE V

Mechanistic studies regarding the 14 kDa fragment

To examine the mechanism by which the 14 kDa fragment inhibits matrix assembly, the ability of this fragment to interact with fibronectin was tested according to the procedure described in Example II. Fibronectin was coated onto plastic wells in concentrations ranging from 0–100 μg/ml, blocked with BSA, then the wells were probed with $^{125}$I-labeled 14 kDa fragment (FIG. 5, panel A) or $^{125}$I-labeled fibronectin (FIG. 5, panel B) for 2 hours at 37° C. The amount of radioiodinated protein bound was measured after washing extensively with 0.2% BSA in PBS. Each data point is the average of duplicate determinations.

Figure 5A:
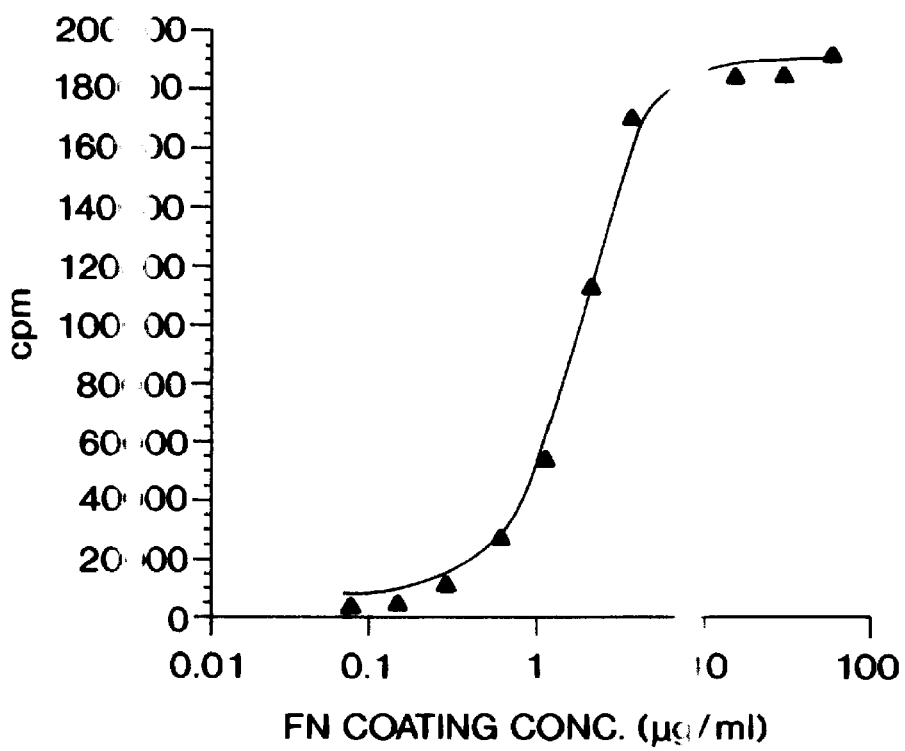
FIG. 5A illustrates the binding of labeled 14 kda fragment to fibronectin.
Figure 5B:
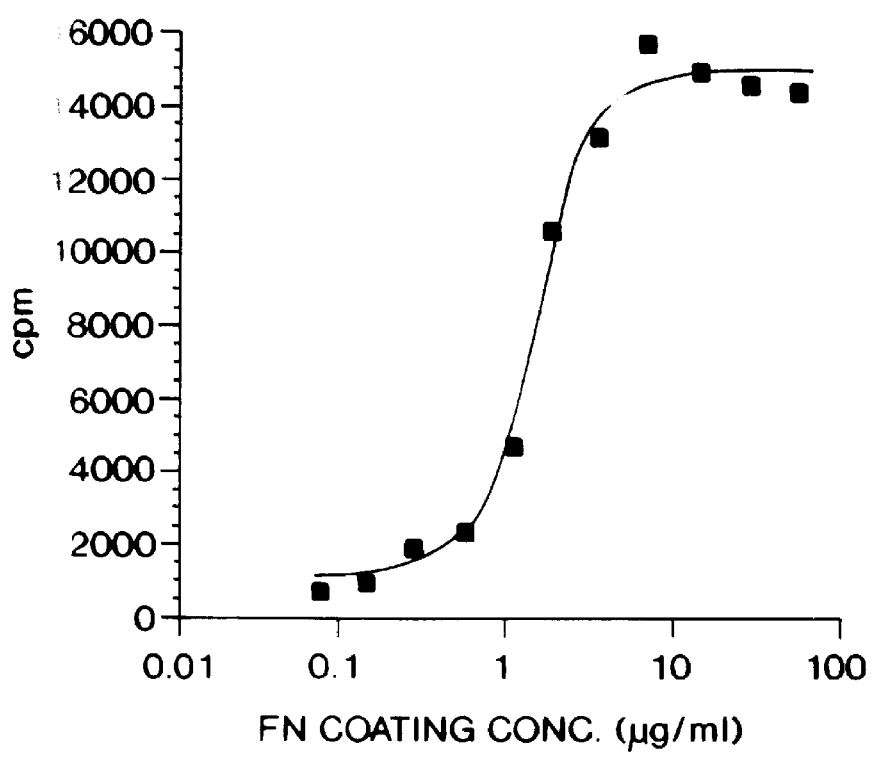
FIG. 5B illustrates the binding of labeled fibronectin to fibronectin.

As shown in FIG. 5, $^{125}$I-fibronectin and 125I-14 kDa fragment both bound to fibronectin coated on the plastic in a dose dependent manner. The total $^{125}$I-14 kDa bound was approximately 10 fold higher than the total amount of $^{125}$I-fibronectin bound, as can be seen by comparing FIG. 5A (14 kDa fragment) to SB (full-length fibronectin). Taking into account the specific activities and the amounts of each protein added, this indicated that the maximal binding of the 14 kDa fragment to fibronectin was 5–10 fold more efficient (on a molar basis) than fibronectin binding to fibronectin.

The ability of the 14 kDa fragment to compete for fibronectin-fibronectin binding was then tested as follows. Plastic wells were coated with 5 μg/ml fibronectin, blocked with BSA, then probed with $^{125}$I-14 kDa (FIG. 6, panel A), or $^{125}$I-fibronectin (FIG. 6, panel B), in the presence of various concentrations of unlabeled 14 kDa (▲) or fibronectin (■). The solutions were incubated for 2 hours at 37° C., followed by extensive washing with 0.2% BSA in PBS, and measurement of the radioactivity bound to the wells. Each data point is the average of duplicate determinations.

Figure 6A:
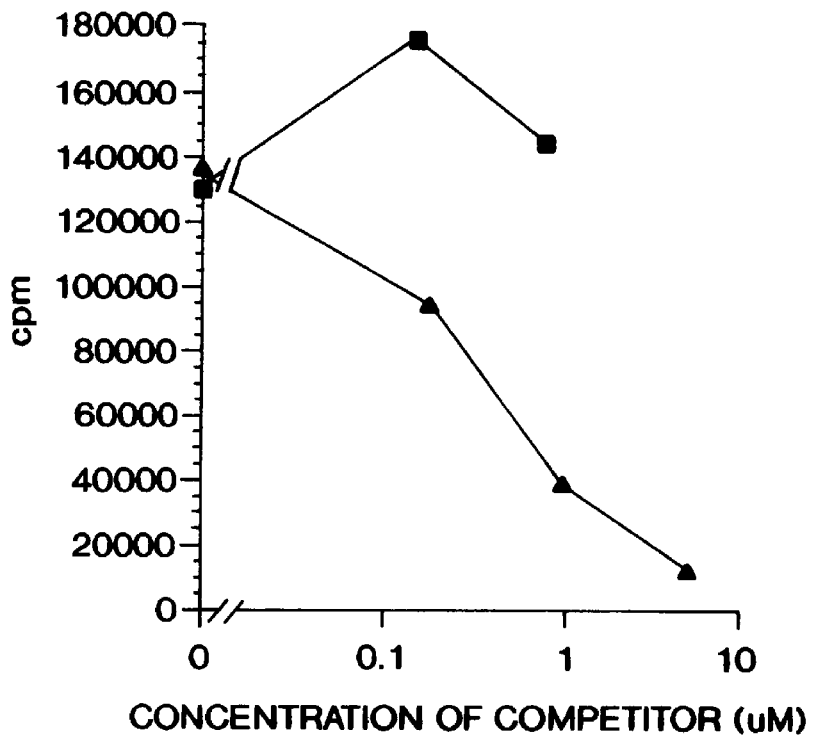
FIG. 6 illustrates competitive inhibition of the 14 kDa fragment (FIG. 6A) and fibronectin (FIG. 6B) for 14 kDa-fibronectin and fibronectin-fibronectin binding sites.

As seen in FIG. 6, the unlabeled 14 kDa fragment competed efficiently for the binding of $^{125}$I-14 kDa fragment to fibronectin, thereby demonstrating the specificity of this binding (FIG. 6A). Yet, unlabeled fibronectin did not compete for the binding of $^{125}$I-14 kDa fragment to fibronectin. One explanation for this is that the unlabeled fibronectin is binding to the fibronectin coating, and that $^{125}$I-14 kDa fragment then binds to either the coated or the adsorbed fibronectin.

Figure 6B:
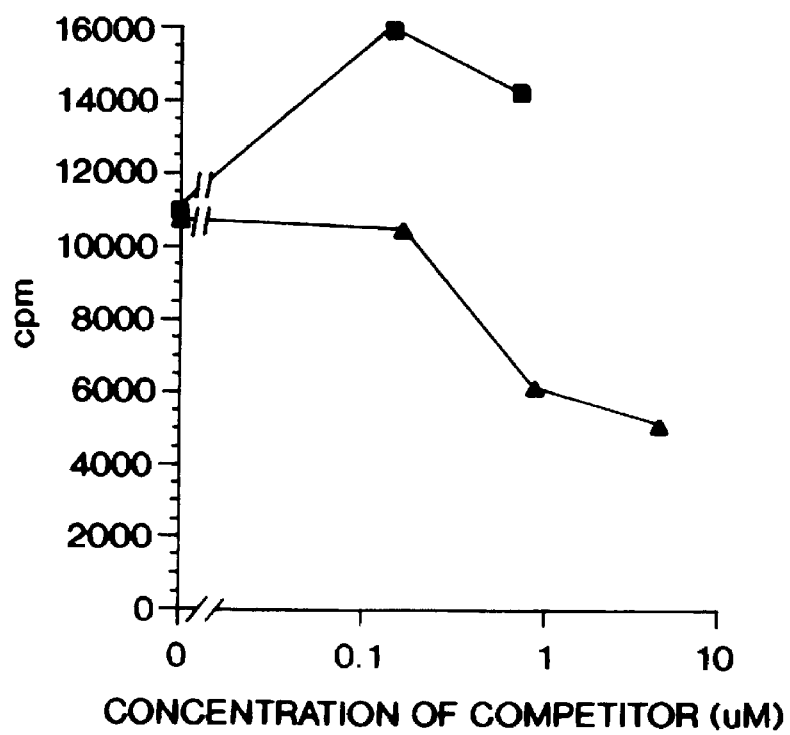

Besides competing for 14 kDa-fibronectin binding, the excess unlabeled 14 kDa fragment also competed for fibronectin-fibronectin binding (FIG. 6B). At the highest concentration tested (5 μM), the 14 kDa fragment inhibited the binding of fibronectin to fibronectin by more than 50%. As with 14 kDa-fibronectin binding, unlabeled fibronectin did not compete for the fibronectin-fibronectin binding, probably for the reasons mentioned above. Thus, the 14 kDa fragment of fibronectin that inhibited matrix assembly, also binds to fibronectin directly, and inhibits fibronectin-fibronectin association.

EXAMPLE VI

Synthetic subfragments of the 14 kDa polypeptide

Four polypeptides (of 30–34 amino acids each) were synthesized, representing the region of fibronectin encompassed by the 14 kDa fragment (polypeptides P1, P2, P3, and P4 ). These polypeptides were tested for inhibition of the 14 kDa-fibronectin association according to the procedure described in Example II as follows. Plastic wells were coated with 5 μg/ml fibronectin, blocked with BSA, then probed with $^{125}$I-labeled 14 kDa fragment (FIG. 7, panel A), or $^{125}$I-labeled fibronectin (FIG. 7, panel B), in the presence of various concentrations of unlabeled heparin-binding fragments (■), polypeptide P1 (●, polypeptide P2 (▲), polypeptide P3 (□), or an α$_5$ cytoplasmic domain polypeptide as a negative control (o). The solutions were incubated for 2 hours at 37° C., followed by extensive washing with 0.2% BSA in PBS, and measurement of the radioactivity bound to the wells. The concentration values shown in FIG. 7 for heparin-binding fragments refer to the final concentrations of the 14 kDa fragment in the solutions.

Figure 7A:
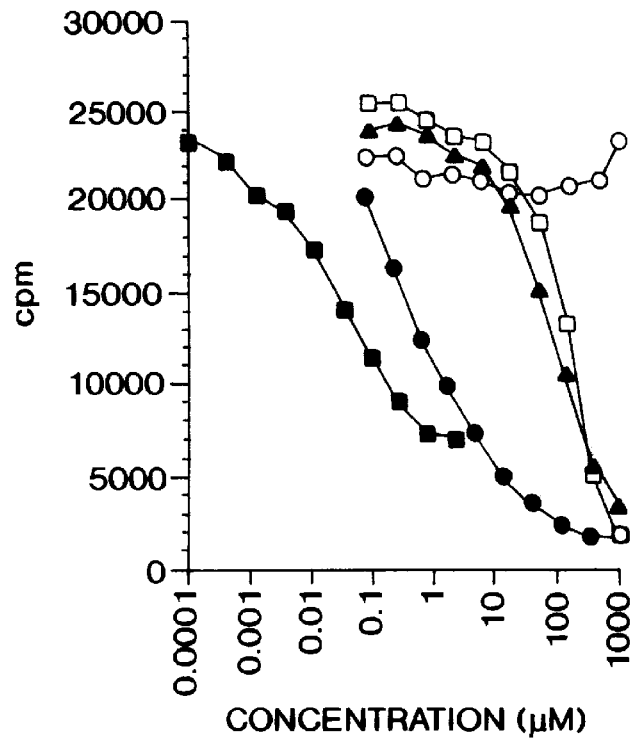
FIG. 7 illustrates the inhibition of 14 kDa fragment-fibronectin binding (FIG. 7A), and fibronectin-fibronectin binding (FIG. 7B) by polypeptides P1, P2 and P3 from the 14 kDa region.
Figure 7B:
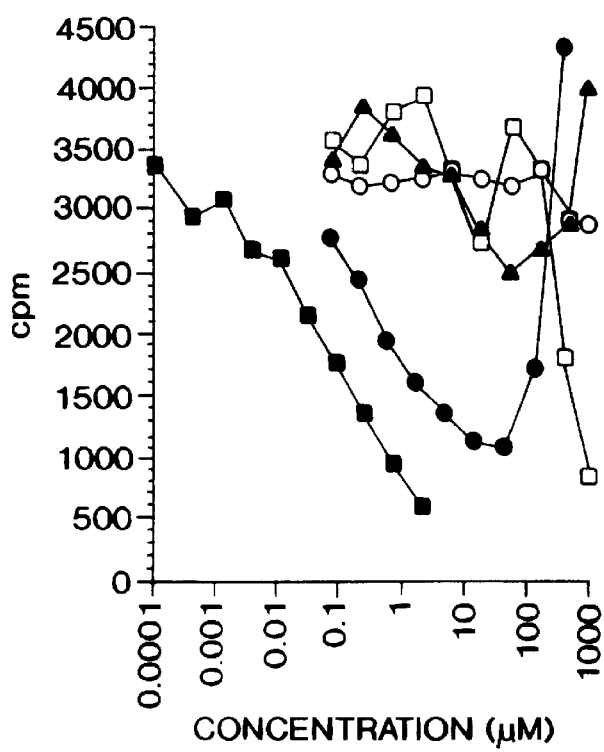

Polypeptide P1 was the most efficient at inhibiting the binding of the 14 kDa fragment to fibronectin, with an IC$_{50}$ of 1 μM; polypeptides P2 and P3 were approximately 100-fold less potent (FIG. 7A). Polypeptide P4 did not significantly inhibit the 14 kDa-fibronectin association, rather, at concentrations above 100 μM, it stimulated this association. The reason for the enhancement of binding by polypeptide P4 is not clear; it is possible that polypeptide P4 represents part of a fibronectin binding domain. As shown in FIG. 7, a non-related polypeptide (a polypeptide representing the cytoplasmic domain of the integrin α$_5$ subunit) had no effect on 14 kDa-fibronectin association.

Since the 14 kDa fragment was found to inhibit fibronectin-fibronectin association, it was next tested whether any of the polypeptides representing the 14 kDa region could also inhibit the binding of fibronectin to itself. Once again polypeptide P1 proved to be the most potent, inhibiting fibronectin self-association with an IC$_{50}$ of approximately 1 μM (FIG. 7B). Polypeptide P3 also significantly inhibited fibronectin-fibronectin binding with an IC$_{50}$ of 200–300 μM (FIG. 7B).

While polypeptide P1 inhibited fibronectin-fibronectin association at low concentrations (0.1 to 50 μM), at high concentrations it actually enhanced the binding of fibronectin to the wells (FIG. 7B). At high concentrations, it has been found that polypeptide P1 aggregates and can be pelleted by high speed centrifugation. This phenomenon does not occur with polypeptide P2. It is possible that at high concentrations polypeptide P1 aggregates into multimers and binds to the coated fibronectin and that the $^{125}$I-fibronectin probe becomes incorporated into these polypeptide P1/fibronectin complexes. This could lead to the observed increase in signal seen with P1 concentrations above 100 μM, because as shown below, fibronectin binds directly to polypeptide P1. Moreover, this explanation was supported by the demonstration that polypeptide P1 could be pelleted by centrifugation from solutions containing more than 100 μM of polypeptide. Thus, the ability of the 14 kDa fragment to inhibit fibronectin-fibronectin binding was also shared by polypeptide P1, which was modeled after the amino terminal 31 residues of the 14 kDa fragment.

The inhibition of fibronectin-fibronectin association by polypeptide P1 implies that P1 binds to fibronectin. To study the binding of fibronectin to P1 or the other polypeptides, the polypeptides were covalently linked to Sepharose beads, and the resins were tested in affinity chromatography assays by using human plasma as a source of fibronectin, according to the procedure described in Example II.

Figure 8:
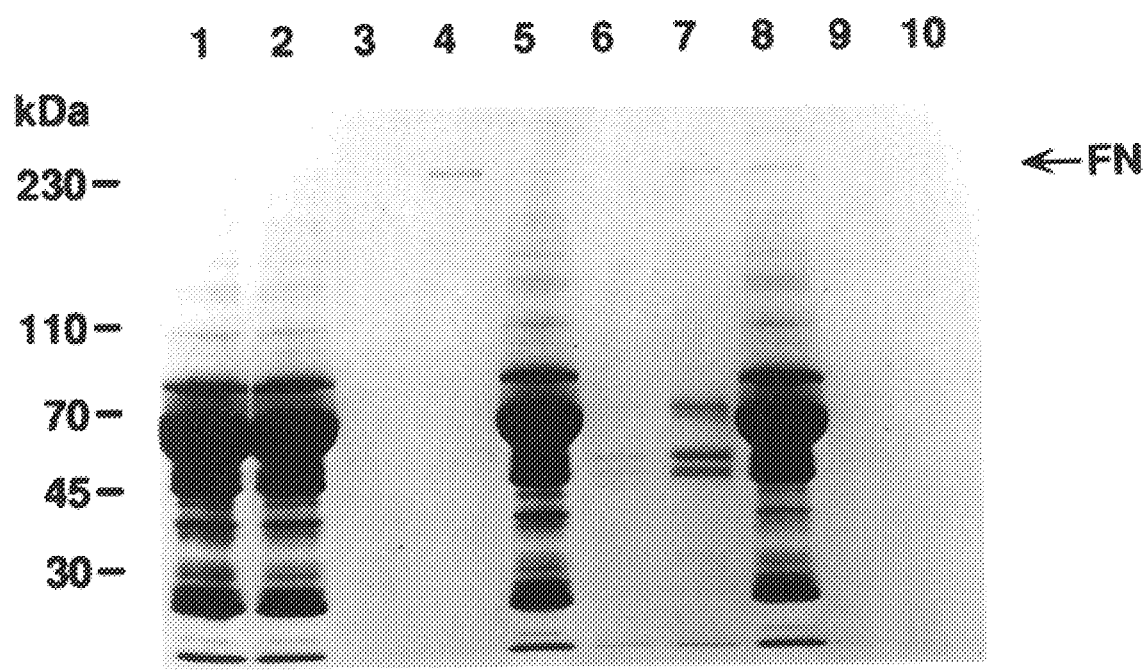
FIG. 8 illustrates the binding of plasma fibronectin to affinity columns made of either gelatin-Sepharose (lanes 2–4), polypeptide P1 (lanes 5–7), or polypeptide P2 (lanes 8–10).

With respect to FIG. 8, human plasma was applied to either gelatin-Sepharose (lanes 2–4) or columns made of polypeptide P1 (lanes 5–7) or P2 (lanes 8–10) coupled to Sepharose. The unbound fraction of proteins was collected, the columns were washed with PBS+5 mM EDTA (PBS/EDTA), followed by 0.2M NaCl in PBS/EDTA. Proteins remaining bound to the columns were eluted with 8M urea in PBS/EDTA. Lane 1 contains starting material. Lanes 2, 5 and 8 are the flow-through fractions from the gelatin, P1, and P2, columns, respectively. Lanes 3–4, 6–7, and 9–10 are the first and second urea eluates from the gelatin, P1, and P2, columns, respectively. The positions of molecular mass standards are indicated to the left of the figure. The position of fibronectin is indicated to the right of the figure.

Upon inspection of FIG. 8, it is seen that most of the fibronectin was removed from plasma by passage over either a gelatin or a P1 column (FIG. 8, lanes 2 and 5). The capacity of the P1 column for fibronectin was comparable to that of gelatin-Sepharose, which is known to be 0.5 mg fibronectin/mg gelatin (Engvall and Ruoslahti, supra). The bound fibronectin was not eluted by 0.3M NaCl, but it was completely removed from both the gelatin and P1 columns by 8M urea (FIG. 8, lanes 3, 4, 6 and 7). A solution of P1 will also elute fibronectin from the P1 column. The preparation eluted from the P1 column with 8M urea (FIG. 8) contained some other plasma proteins, but was greatly enriched in fibronectin. This indicates that fibronectin binds efficiently to polypeptide P1.

There is yet a third similarity between polypeptide P1 and the 14 kDa fragment. Confluent monolayers of IMR-90 cells were incubated with $^{125}$I-fibronectin in the presence of various concentrations of unlabeled fibronectin (■), polypeptide P1 (●), or polypeptide P2 (▲), according to the procedure described in Example II. In panel A of FIG. 9, cells were incubated for one hour, washed, and the total bound radioactivity was measured. In panel B of FIG. 9, cells were incubated for 24 hours, washed, and the total amount of $^{125}$I-fibronectin was measured. Each data point is the average of duplicate determinations.

Figure 9A:
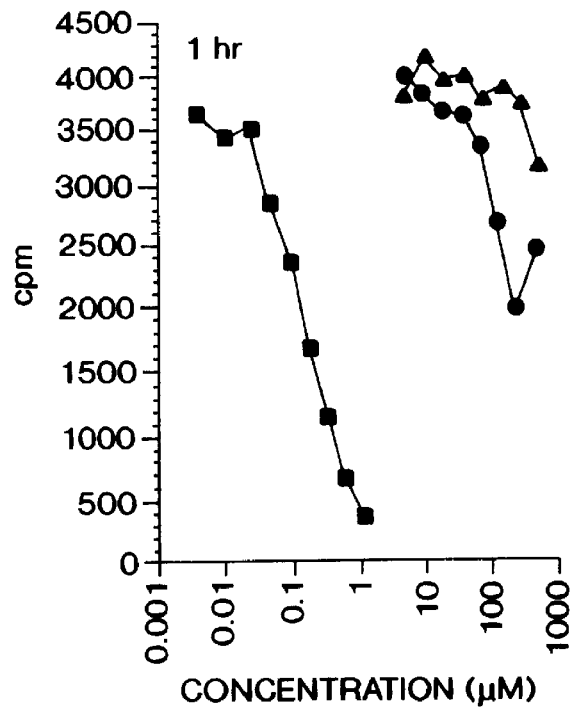
FIG. 9 illustrates the inhibition of fibronectin matrix assembly by fibronectin, polypeptide P1, and polypeptide P2, after one hour (FIG. 9A), or after 24 hours (FIG. 9B).

Testing of polypeptides P1 to P4 in the 1 hour matrix assembly assay showed that, among the four polypeptides, polypeptide P1 inhibited the binding of $^{125}$I-fibronectin to cells most efficiently, by approximately 40–50% (FIG. 9A). The other polypeptides also were somewhat effective in the 1 hour assay, typically inhibiting by approximately 25% (the result for P2 is shown in FIG. 9A). The effect of the se polypeptides is not as pronounced as that of the well-known effect of the 70 kDa fragment at preventing fibronectin binding to cells, as noted in the literature.

Figure 9B:
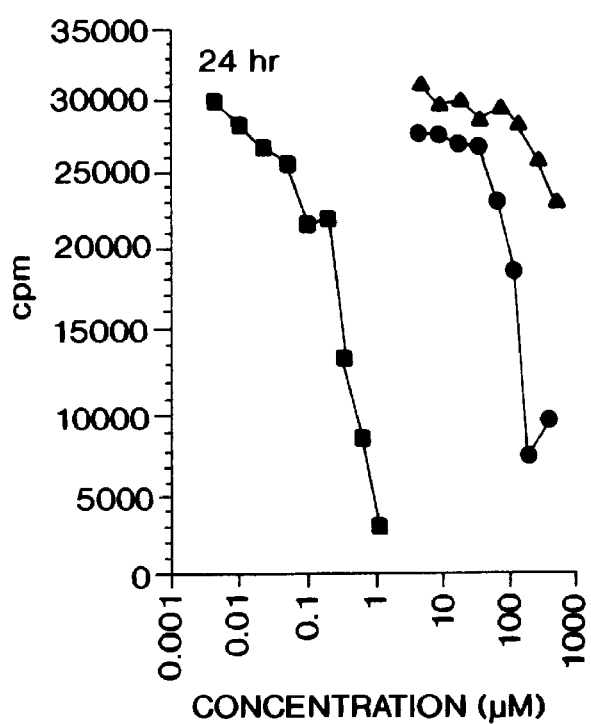

As with the 14 kDa fragment, polypeptide P1 dramatically reduced the incorporation of fibronectin into the matrix in a 24 hour assay (FIG. 9B). Maximal inhibition of the incorporation of fibronectin into the matrix by approximately 80% was obtained at a polypeptide P1 concentration of 250–500 μM.

Cells that were treated with polypeptide P1 at concentrations above 500 μM exhibited an unusually high level of $^{125}$I-fibronectin signal in the matrix assembly assay. As mentioned above, polypeptide P1 tended to aggregate at high concentrations. It is possible that at concentrations above 500 μM polypeptide P1 aggregated on cell surfaces, or onto the plastic surface, and the thereby caused adsorption of $^{125}$I-fibronectin.

To determine whether polypeptide P1 and the 70 kDa fragment could cooperate in the inhibition of matrix assembly, mixing experiments were done by treating cells with a constant amount of unlabeled 70 kDa (0.03 μM), and adding various amounts of polypeptide P1 (from 0–500 μM). In the presence of the 70 kDa fragment, the maximal inhibition by polypeptide P1 was obtained at a concentration of 250–500 μM. Thus, the re was no increase in the effective concentration for inhibition by polypeptide P1 in the presence of the 70 kDa fragment and the combined effect was additive, not synergistic.

The data presented above demonstrate that polypeptide P1 inhibits matrix assembly in a manner similar to that of the 14 kDa fragment. Both the 14 kDa fragment and polypeptide P1 have a small effect on the binding of fibronectin to cell surfaces, but both significantly inhibit the incorporation of fibronectin into the extracellular matrix.

EXAMPLE VII

Effect of 14 kDa polypeptide on endogenous fibronectin matrix assembly

All of the experiments presented thus far have focused on the assembly of exogenous fibronectin into the matrix. The effect of the 14 kDa polypeptides on endogenous fibronectin matrix assembly has also been studied. Endogenous fibronectin matrix assembly is the matrix made from fibronectin that is synthesized by the cells during the period of the assays, whereas exogenous matrix assembly is matrix made from fibronectin that is added to the cell culture. Exogenous fibronectin is not synthesized by the cells during the assay.

The following experiment was performed. IMR-90 cells were seeded onto Lab-Tek 8 well Chamber slides which had been precoated with 50 μg/ml collagen type I to enhance the attachment of cells to the wells. After attaching for 1 hour at 37° C., cells were washed once with α-MEM plus 10% fibronectin-deficient FCS, the n cultured for 48 hours in 10% fibronectin-deficient medium plus either no additions (A), or 1 mg/ml 70 kDa fragment (B), or 500 μM polypeptide P1 (C), or 500 μM polypeptide P2 (D). Cells were then fixed with 3.7% paraformaldehyde, 60 mM sucrose, in PBS, pH 7.4 for 30 minutes at room temperature. Cell layers were washed three times with 0.2% BSA in PBS, then stained with 10 μg/ml of affinity-purified, rhodamine labeled rabbit anti-human fibronectin antibodies as described above. The panels in FIG. 10 show representative fields from each culture (A) through (D). The bar in FIG. 10 equals 25 μm.

Figure 10A:
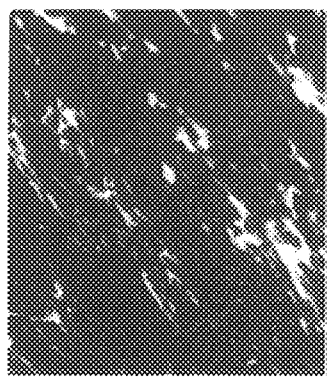
FIG. 10 illustrates effect on endogenous fibronectin matrix assembly with no additions (FIG. 10A), the addition of the 70 kDa fragment (FIG. 10B), polypeptide P1 (FIG. 10C), or polypeptide P2 (FIG. 10D).
Figure 10B:
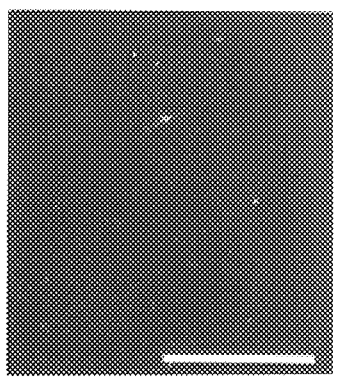
Figure 10C:
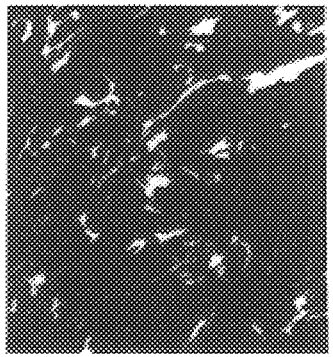
Figure 10D:
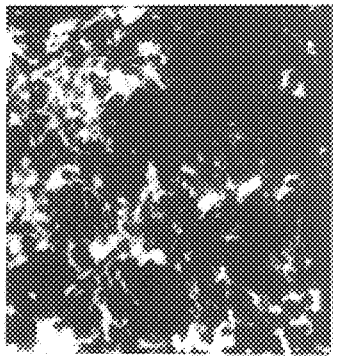

Shortly after seeding, cells were grown in the presence of various concentrations of the 70 kDa fragment, or polypeptides P1 or P2 for 48 hours. As shown previously, see McDonald et al., supra, high concentrations of the 70 kDa fragment inhibited endogenous matrix assembly (FIG. 10B). Subconfluent cultures were studied because it has been found that the effect of the polypeptides on matrix assembly was more pronounced in subconfluent cultures than in confluent cultures. Polypeptide P1 was the most effective at disrupting endogenous fibronectin matrix assembly. As seen in FIG. 10C, in the presence of polypeptide P1 only short stitches of matrix were seen on the cells, and those stitches were usually located at the edges of cells, with little or no fibrils located above or beneath the cell bodies. However, in the presence of polypeptide P2 an extensive matrix surrounded the cells (FIG. 10D). Thus polypeptide P1 disrupted endogenous fibronectin matrix assembly, while polypeptide P2 did not.

EXAMPLE VIII

Promotion of cell attachment

To determine whether fibronectin which is bound to polypeptide P1 is capable of supporting cell adhesion, plastic wells were coated with polypeptide P1, the n fibronectin in solution was bound to the coated polypeptide, and cells were seeded onto this substrate to assay the extent of cell adhesion. Two experiments were then performed.

In the first experiment, polypeptide P1 and a control polypeptide (representing the cytoplasmic domain of the integrin $\alpha_4$ subunit) were coated onto plastic wells at various concentrations in the presence of 0.1M $Na_2CO_3$, pH 9.5, and 0.25% glutaraldehyde. The wells were then blocked with 1% BSA in PBS, followed by the addition of 250 µg/ml of fibronectin, 1% BSA, in PBS. After incubation of this solution of fibronectin and BSA for 3 hours, the wells were washed, and IMR-90 cells were seeded onto the dishes for one hour at 37° C. in media lacking calf serum.

Figure 11A:
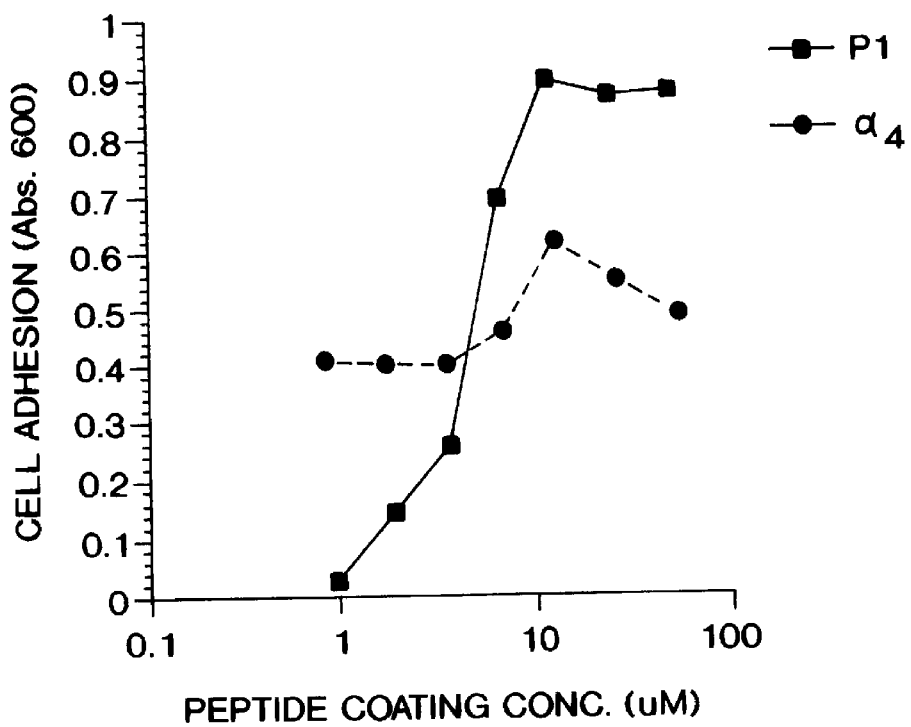
FIG. 11 illustrates the variation in cell attachment to fibronectin which is bound to a polypeptide P1-coated or $\alpha_4$ coated-substrate as the concentration of polypeptide (FIG. 11A) is increased, or as the concentration of fibronectin (FIG. 11B) is increased.
Figure 11B:
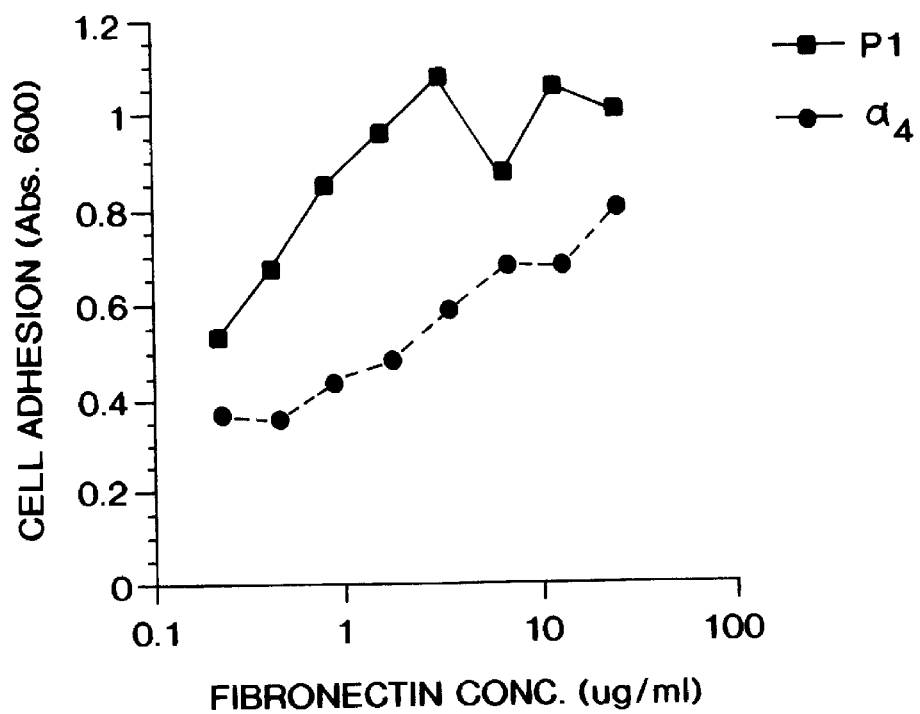

The degree of cell attachment was quantitated by staining cells with 0.5% Crystal Violet, 50% ethanol, and measuring the amount of dye bound to the cells in the wells. As shown in FIG. 11, panel A, polypeptide P1 supported cell adhesion in a dose dependent manner after binding fibronectin. When no polypeptide was coated onto the dish, no cell adhesion was detected, indicating that polypeptide P1 was required for cell adhesion. The control polypeptide gave a relatively high background (as can be seen by the amount of cell adhesion even at low levels of polypeptide $\alpha_4$ coating), and did not support significantly greater cell adhesion at higher levels of polypeptide coating, indicating a non-specific adhesion of cells to the wells coated with the $\alpha_4$ polypeptide.

In the second experiment, a constant concentration (1 mM) of polypeptide PI (or $\alpha_4$) was coated onto the plastic wells, the wells were blocked with 1% BSA, and the n various concentrations of fibronectin in 1% BSA were incubated for 3 hours with the polypeptide-coated wells. After washing the wells, IMR-90 cells were seeded onto the wells and the degree of cell adhesion was determined as described above. As shown in FIG. 11, panel B, polypeptide P1 supported a higher degree of cell adhesion than did polypeptide $\alpha_4$. This cell adhesion required incubation with fibronectin, since the degree of cell adhesion was directly related to the concentration of fibronectin in solution.

The above data indicate that fibronectin binds to polypeptide P1 which is coated onto a substrate, and that the bound fibronectin is capable of supporting cell adhesion, thereby demonstrating that polypeptide is useful for promoting cell attachment.

EXAMPLE IX

Locating a Second Binding Site which binds to the P1 Polypeptide

Figure 13A:
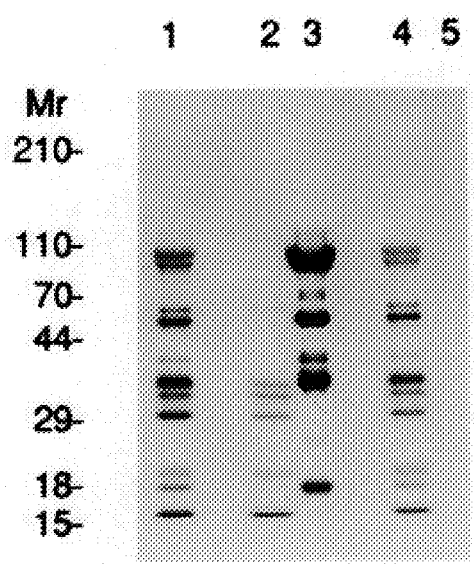
FIG. 13A illustrates the binding of cathepsin-D digested fragments of fibronectin to P1-Sepharose or P2-Sepharose columns.

To locate a second fibronectin binding site which binds to the first binding site contained in the $III_1$ repeat, fibronectin ( 2 mg/ml) was digested with cathepsin-D and the non-gelatin binding fragments were applied to 1 ml affinity columns in 5 ml aliquots. The columns were run and eluted as described in Example I. The columns contained either the active $III_1$ polypeptide P1, derived from $III_1$, or polypeptide P2, which is also derived from $III_1$ but inactive in fibronectin-fibronectin binding assays, as described above in Example VI. Fractions were run on a gel under reducing conditions and stained with Coomassie blue (FIG. 13A). The positions of molecular mass standards are indicated to the left of the gel. Lanes 2 and 4 show the unbound fractions, and lanes 3 and 5 show the bound fractions from the P1 and P2 columns respectively. As can be seen in FIG. 13A, lane 3, P1-Sepharose bound fragments ranging in size from 18 kDa to 120 kDa. The fragments that bound to P1-Sepharose bound with high avidity; the unbound fraction was essentially devoid of these fragments (lane 2). On P2-Sepharose essentially all of the fragments were in the unbound fraction (FIG. 13A, lane 4). Thus, several of the cathepsin-D fragments of fibronectin bound specifically to P1-Sepharose and not to P2-Sepharose.

Figure 13B:
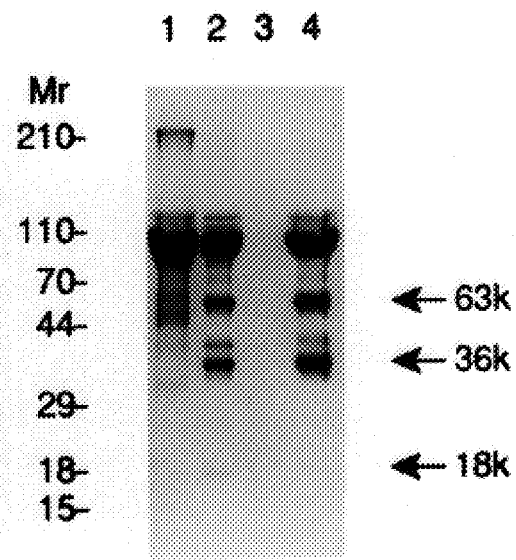
FIG. 13B illustrates the binding of fragments which bound to P1-Sepharose to a second P1-Sepharose column after reduction and alkylation of the fragments.

The fragments which bound to P1-Sepharose (lane 3) were then subjected to reduction and alkylation according to the procedure described in Example I. The reduced and alkylated fractions were the n reapplied to a P1-Sepharose column. The bound and unbound fragments were run on a gel under non-reducing conditions. The proteins were stained with Coomassie blue, and the positions of the molecular mass standards are indicated to the left of the gel. FIG. 13B shows the P1-binding fragments before (lane 1) and after (lane 2) reduction and alkylation. Lane 3 shows the unbound fraction from the reapplied material, and lane 4 shows the bound fraction. The positions of a 63 kDa, 36 kDa, and 18 kDa fragment which bind to the P1 column are indicated to the right of the gel in FIG. 13B.

Analysis of the P1-binding fragments before (FIG. 13B, lane 1) and after (FIG. 13B, lane 2) reduction and alkylation indicated many of the fragments contained disulfide bonds. Therefore some of the fragments that bound to P1-Sepharose may have bound only because they were cross-linked to fragments with binding activity. When reduced and alkylated P1-binding fragments were reapplied to a P1-Sepharose column most of the fragments that had originally bound retained the binding activity (FIG. 13B, lane 4), except that a few less abundant fragments were now in the unbound fraction (FIG. 13B, lane 3). In a separate experiment it was found that several of the fragments remained bound to PI-Sepharose even after washing the column with 1M urea. In particular, the 18 kDa fragment required 3 to 4M urea for elution, whereas the other fragments eluted between 1 and 3 M urea (not shown). That disulfide bonds were not required for the binding suggests that the binding site may be a linear sequence.

Three of the P1-binding fragments, the 63 kDa, 36 kDa, and the 18 kDa fragments were further analyzed by amino-terminal sequencing as described in Example I. The amino terminal residue of the 63 kDa fragment corresponds to amino acid number 1583 (according to the number system of Kornblihtt et al., (1985) supra), which is in the 11th type III repeat of EDa+, EDb−(Extra Domains a and b) fibronectin as shown in FIG. 14. EDa+and EDb−refers to two extra type III repeats that are spliced into the fibronectin molecule. The amino termini of the 36 kDa and 18 kDa fragments correspond to amino acid numbers 2022 and 2154, respectively. These fragments start in the IIICS module, and in the middle of the 10th type I repeat, respectively as seen in FIG. 14. FIG. 14 shows the diagram of fibronectin outlining the locations of the recombinant 14 kDa fragment, the amino-terminal 70 kDa fragment, the cell-binding RGD tripeptide, and the regions represented by the 63 kDa, 36 kDA, and 18 kDa P1-binding fragments. The amino terminal sequenced obtained from the fragments are shown underneath each fragment. These are AQNPS (Sequence ID No. 17) for the 63 kDa fragment, EEHGF for the 36 kDa fragment (Sequence ID No. 18), and AVGDE (Sequence ID No. 19) for the 18 kDa fragment. The three repeating units of fibronectin are depicted as follows: type I repeats (circles), type II repeats (diamonds), and type III repeats (squares). The IIICS regions is depicted by a shaded oval.

The sizes of these three fragments, along with the finding that the se fragments were not detected in the non-reduced samples of P1-binding fragments, indicate that all three of the fragments are likely to extend to the carboxy terminus where the fibronectin molecule is dimerized through disulfide bonds. Thus, the region that these three fragments share is the region encompassed by the 18 kDa fragment; type I repeats 11, 12, and half of number 10. These results indicate that the site that binds to P1 is contained in the carboxy-terminal type I repeats of fibronectin.

Figure 15A:
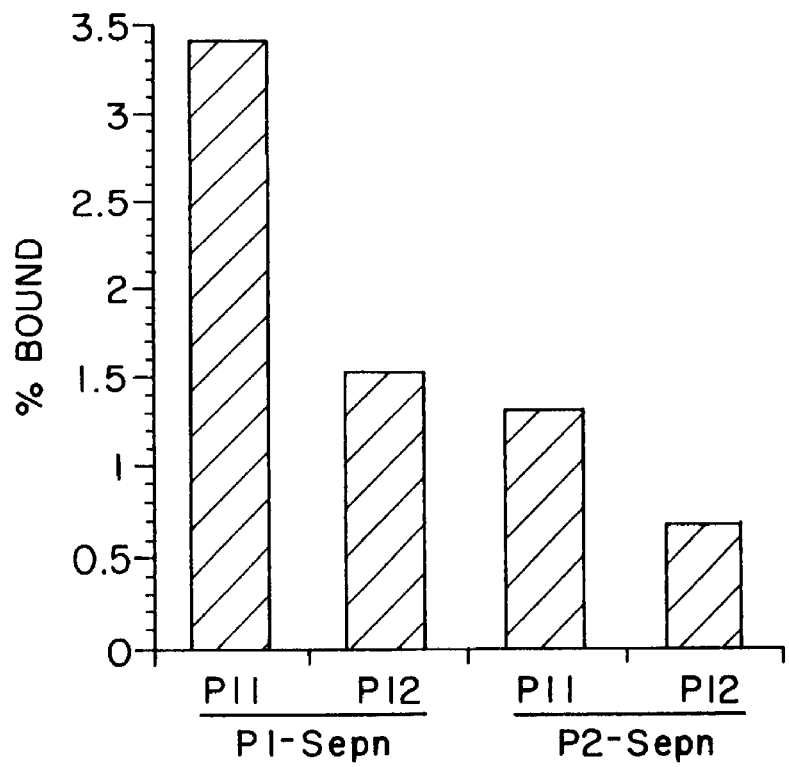
FIG. 15A illustrates the binding of P11 and P12 to P1-Sepharose and P2-Sepharose columns.

In order to localize further the P1-binding site, polypeptides representing the entire 11th type I repeat and the entire 12th type I repeat were synthesized at the Protein Chemistry Laboratory at the La Jolla Cancer Research Foundation after being purified by reverse phase HPLC. These polypeptides are referred to as P11 (representing the 11th type I repeat) and P12 (representing the 12th type I repeat) respectively. The sequence of P11 is RWSHDNGVNY KIGEKWDRQG ENGQMMSSTS LGNGKGEFKS DPHE (Sequence ID No 6), and the sequence of P12 is ATSYDDGKTY HVGEQWQKEY LGAISSSTSF GGQRGWRSDN SR (Sequence ID No 7). The cysteines in the sequence of the type I repeats have been replaced by serines in the synthetic polypeptides P11 and P12. The P11 and P12 polypeptides were applied to 1 ml P1-Sepharose and P2-Sepharose affinity columns. 2 ml of 500 µg/ml solutions of P11 and P12 were applied to each column. FIG. 15A shows the total percentage of starting material that bound to each column. As shown in FIG. 15A, the most efficient binding was between polypeptide P11 and Pi-Sepharose. Neither P11 nor P12 bound well to P2-Sepharose, and the binding of P12 to P11-Sepharose was less than half as efficient as the binding of P11 as seen in FIG. 15A.

Figure 15B:
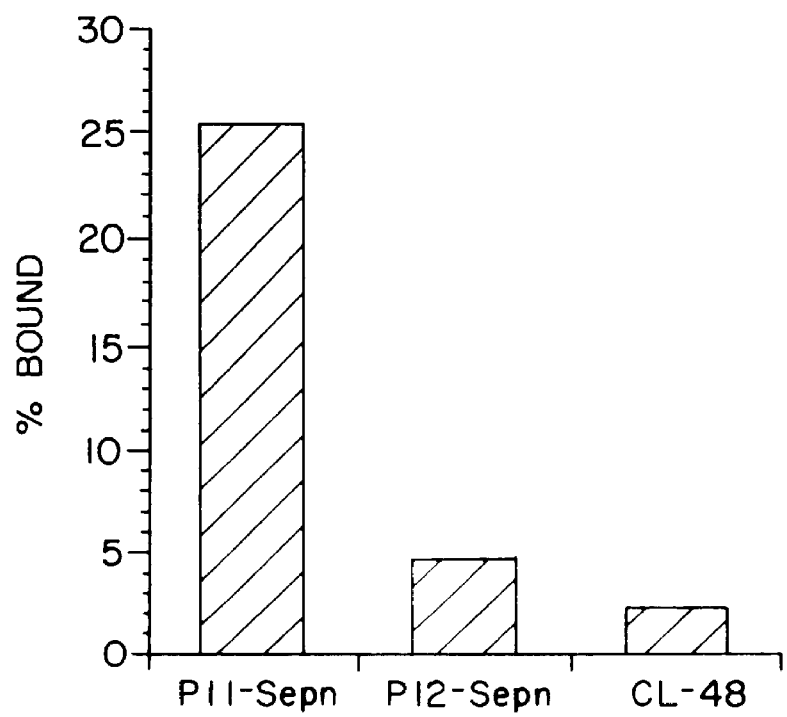
FIG. 15B illustrates the binding of the recombinant $III_1$-E polypeptide to P11-Sepharose, P12-Sepharose, and Sepharose CL-4B columns.

In a reciprocal experiment, the IIIT$_1$-E protein which contains most of the III$_1$ module, was applied to affinity columns made of P11-Sepharose or P12-Sepharose. 1 ml of a 250 µg/ml solution was applied to 0.5-ml columns. The results are shown in FIG. 15B. Approximately 25% of the protein added to the columns bound to P11-Sepharose, while only 4.8% bound to P12-Sepharose, and 2.3% bound to a Sepharose CL-4B column used as a control as seen in FIG. 15B. The results of both affinity chromatography experiments indicate that the P1-binding site is located in the 11th type-I repeat.

EXAMPLE X

Effect of P11 on Fibronectin-Fibronectin Binding and the Binding of the III$_1$-E polypeptide to Fibronectin If the binding site which binds the P1 polypeptide (repeat III$_1$) is contained in either P11 or P12, one would expect one of the se polypeptides to inhibit the binding of one of the 14 kDa fragment-derived polypeptides such as III$_1$-E to fibronectin as well as fibronectin-fibronectin binding. The following experiments were performed to address this hypothesis according to the procedure described in Example II. Plastic wells were coated with 4 µg/ml fibronectin, blocked with BSA, the n probed with $^{125}$I-III$_1$-E (A), or $^{125}$I-fibronectin (B) in the presence of various concentrations of unlabeled fibronectin (●), III$_1$-E (o), polypeptide P1 (Δ), polypeptide P11 (■), or polypeptide P12 (□). The solutions were incubated for 24 hours at 37° C., followed by extensive washing with PBS, and measurement of the radioactivity bound to the wells. Each data point is the average of duplicate determinations.

As shown in FIG. 16A, polypeptide P11 inhibited III$_1$-E-fibronectin binding at concentrations above 10 µM. Polypeptide P11 was approximately 500-fold less potent in this inhibition assay than III$_1$-E, and 50-to 100-fold less potent than polypeptide P1 on a molar basis.

Figure 16B:
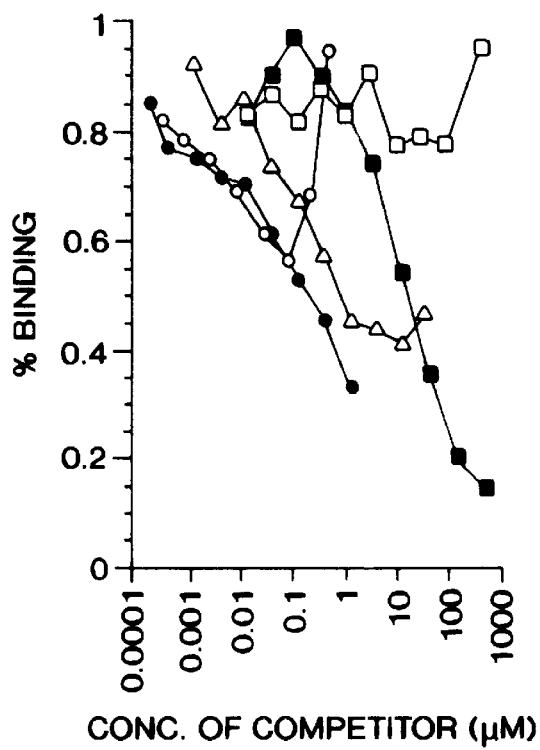

Polypeptide P11 also inhibited fibronectin self-association at concentrations above 10 µM, as seen in FIG. 16B. Polypeptide P11 inhibited fibronectin-fibronectin binding at all concentrations above 10 µM. This is in contrast to the biphasic nature of the effects of III$_1$-E and polypeptide P1 on fibronectin-fibronectin binding; they inhibit the binding at low concentrations, yet enhance binding at higher concentrations as can be seen in FIG. 16B. The biphasic nature of the effects of IIII$_1$-E kDa and polypeptide P1 result in maximal levels of inhibition of no more than 50 to 60%, whereas, polypeptide P11 can inhibit fibronectin-fibronectin binding by as much as 80%.

EXAMPLE XI

Characterization of Fibronectin-Fibronectin Binding Sites

Figure 17A:
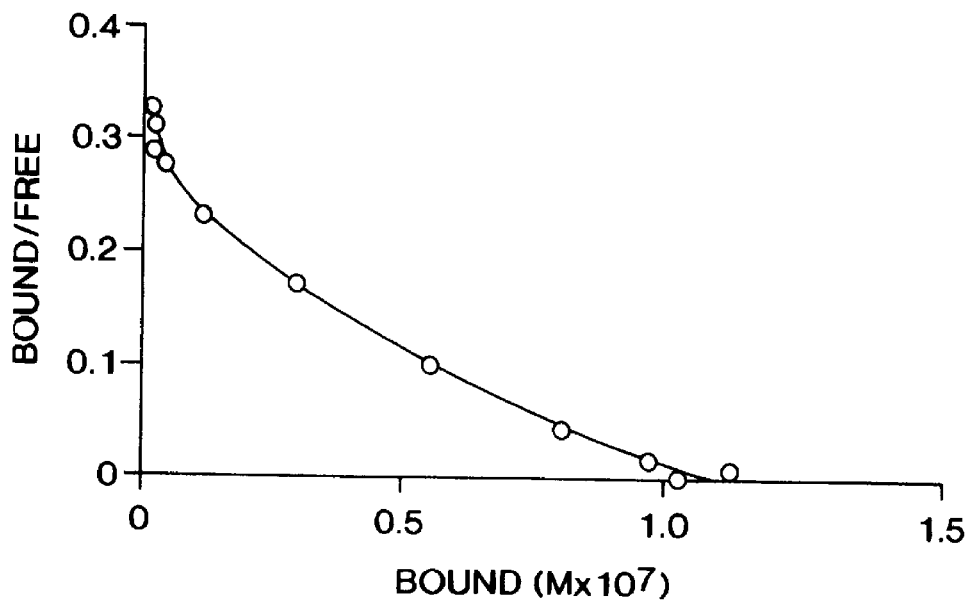
FIG. 17 illustrates Scatchard plot analysis for $III_1$-E-fibronectin binding (FIG. 17A) and fibronectin-fibronectin binding (FIG. 17B).
Figure 17B:
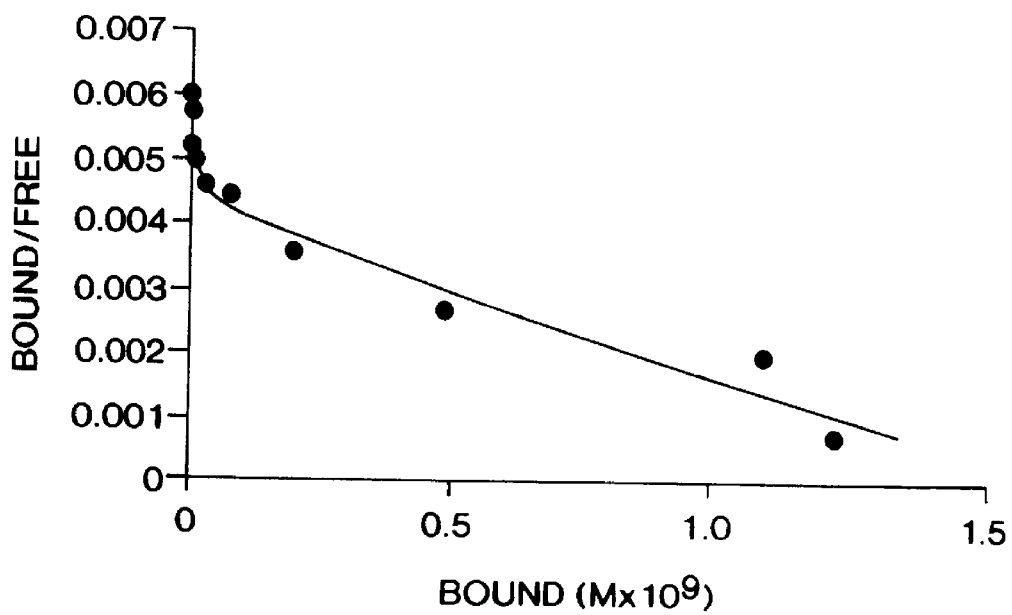

Since III$_1$-E and P1 polypeptide binds to the I$_{11}$ repeat section in fibronectin, data from several binding experiments were used to determine the affinity of III$_1$-E for fibronectin, and of fibronectin for fibronectin. The binding data from the experiment shown in FIG. 16 was analyzed with the aid of the program LIGAND. The Scatchard curve derived from the competition of III$_1$-E-fibronectin binding by unlabeled III$_1$-E is shown in 17A. The curve derived from the competition of fibronectin-fibronectin binding by unlabeled fibronectin is shown in 17B. In both cases the binding data best fit a model with two classes of binding sites, one high affinity, low abundance site, and one low affinity, higher abundance site. The K$_D$ of the high affinity site for the III$_1$-E-fibronectin binding was 6×10$^{-8}$M with approximately 1–2 binding sites per fibronectin dimer, and the K$_D$ of the low affinity site was 6×10$^{-7}$M, with approximately 10 binding sites per fibronectin dimer, as determined from the Scatchard plot shown in FIG. 17A. Fibronectin-fibronectin binding results also indicated binding to two classes of sites. In this case, the high affinity site had a K$_D$ of 8×10$^{-9}$M, with 1 to 2 binding sites per 1000 fibronectin dimers, while the low affinity site had a K$_D$ of 8×10$^{-7}$M, with 1 to 2 sites per fibronectin dimer as shown in FIG. 17B. The difference in number of binding sites in fibronectin for the III$_1$-E in comparison to fibronectin (ten-fold more low affinity sites and 1000-fold more high affinity sites) may be attributed to the possible masking of binding sites in soluble fibronectin due to the folding of the amino terminus of fibronectin over the III$_1$ region.

Figure 18:
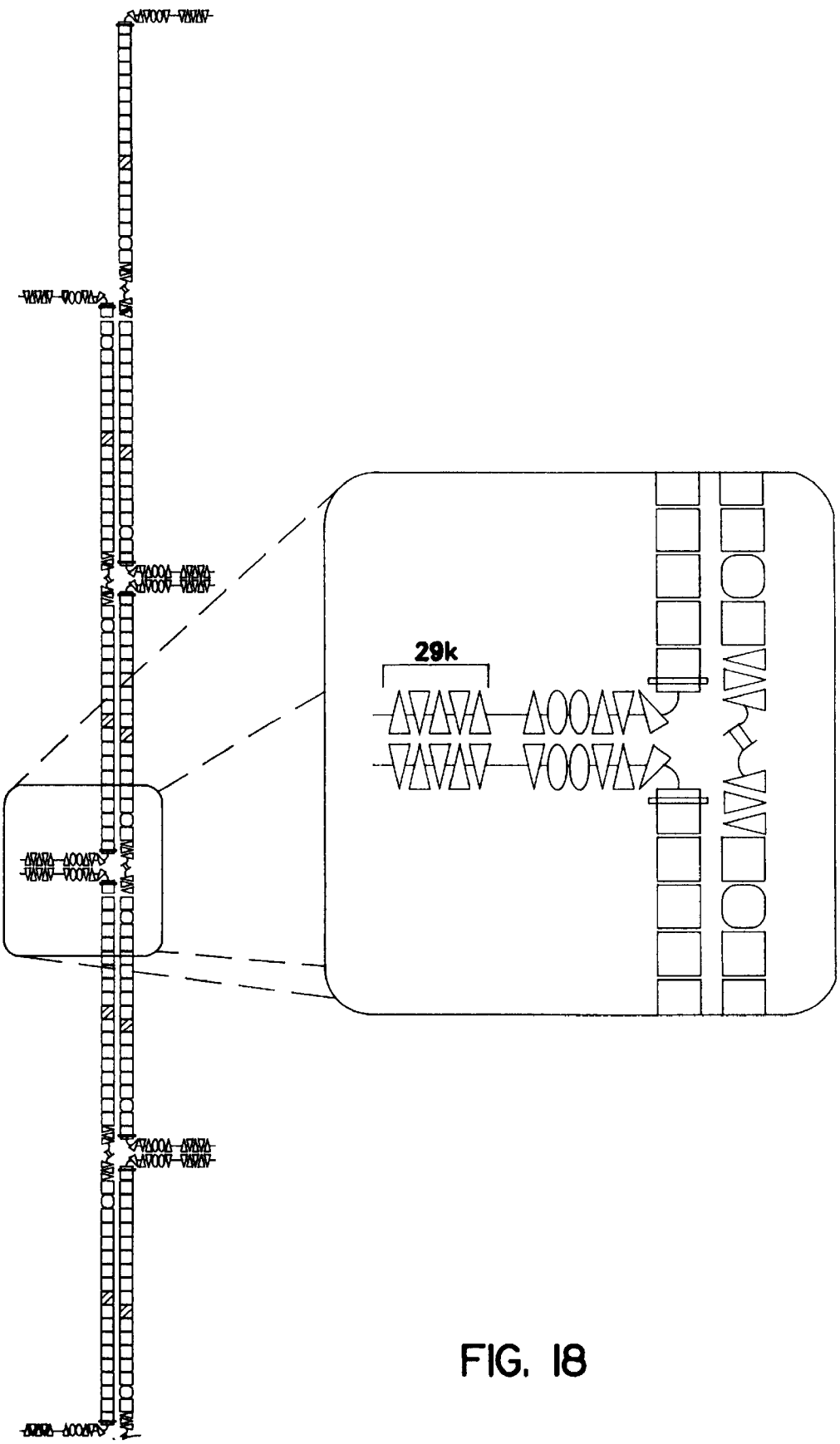
FIG. 18 illustrates a proposed model of fibronectin fiber structure.

The results of Examples IX through XI demonstrates that the fibronectin binding site in the first type III (III$_1$) repeat of the amino-terminal portion of fibronectin binds to the 11th type I (I$_{11}$) repeat near the carboxy terminus of fibronectin and that a polypeptide representing I$_{11}$ (P11) inhibits fibronectin self-association. The importance of the interaction between the I$_{11}$ repeat and the III$_1$ repeat in fibronectin matrix assembly is demonstrated in the above Examples, where polypeptides derived from the III$_1$ and I$_{11}$ sites are shown to inhibit fibronectin self-assembly, which is likely to be a crucial step in matrix assembly. Furthermore, the Scatchard plot analysis indicates that fibronectin self-association occurs through multiple sites of interaction. According to this model, the dimeric nature of fibronectin would allow the amino terminal regions of two molecules to be brought together by having the III$_1$ repeat bind to the I$_{11}$ repeat of a third molecule. This model is shown in FIG. 18, which illustrates the alignment of fibronectin molecules to one another in a fiber. The repeating units of fibronectin are depicted as follows: type I repeats, triangles; type II repeats, ovals; type III repeats, squares. The III$_1$ repeat is shaded with a black stripe indicating the location of the P1 regions. The I$_{11}$ repeat is shown as a black triangle. The type III repeat that contains the RGD cell-binding tripeptide and the IIICS module are shown as a striped square and a rounded rectangle, respectively. The location of the amino-terminal 29 kDa region is also shown. As can be seen in FIG. 18, the model requires that the amino terminus fold away from the backbone of the fibril as shown. Such folding would allow for the binding of the adjacent amino termini to one another. This model would predict that the intermolecular disulfide bond that is formed during matrix assembly would cross-link the amino termini of two molecules together.

EXAMPLE XII

Stimulation of In Vitro Disulfide Cross-Linking of Fibronectin by QE-C

Figure 19:
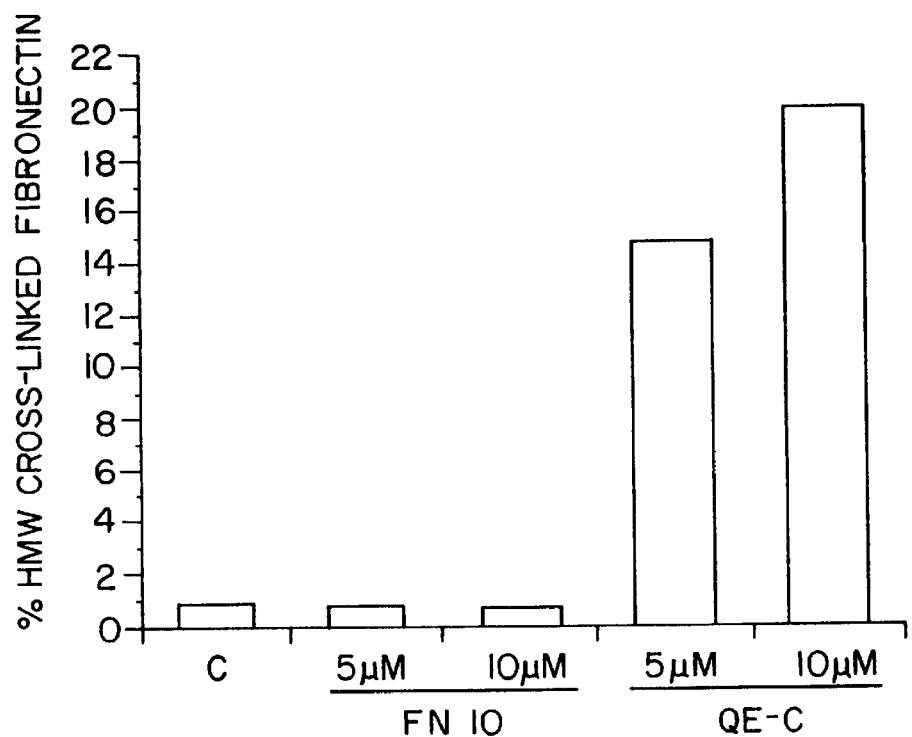
FIG. 19 illustrates the induction of disulfide cross-linking of fibronectin by the QE-C recombinant polypeptide, resulting in an increase in the number of high molecular weight aggregates (HMW cross-linked fibronectin).

Since polypeptides and recombinant proteins from the III$_1$ region were able to enhance fibronectin-fibronectin binding at higher concentrations, another assay was used to determine whether such a protein could stimulate in vitro disulfide cross-linking of fibronectin, in the absence of cells, according to the procedure described in Example II. $^{125}$I-fibronectin was incubated with various concentrations of either QE-C, or FN 10 (a negative control recombinant protein encompassing the 10th type III repeat in fibronectin as described in Example II), and the extent of disulfide cross-linking that resulted in the formation of high molecular weight (HMW) aggregates of fibronectin was determined. As shown in FIG. 19, the FN 10 protein had no effect on the degree of fibronectin disulfide cross-linking; the amount of HMW aggregates was no higher in the FN 10 samples than in the control sample receiving no additional protein. However, in the presence of QE-C the re was a dramatic induction of disulfide cross-linking of fibronectin. In the presence of 10 μM QE-C approximately 20% of the fibronectin in the sample was present in HMW aggregates. This indicates that QE-C is able to cause the disulfide cross-linking of fibronectin to HMW aggregates, even in the absence of cells or any other proteins (except for the BSA that served as a carrier protein in all of the samples). This also indicates that QE-C may be able to nucleate fibronectin fibrillogenesis, since this process is characterized by the disulfide cross-linking of fibronectin into HMW aggregates.

EXAMPLE XIII

Enhancement of Fibronectin Matrix Assembly by III$_1$-C

Since the polypeptides derived from the III1 region of fibronectin were able to enhance fibronectin-fibronectin binding in vitro, and were able to induce fibronectin disulfide cross-linking in vitro, tests to determine whether such recombinant fragments would have an effect on fibronectin matrix assembly when added to cells in tissue culture were performed.

Figure 20:
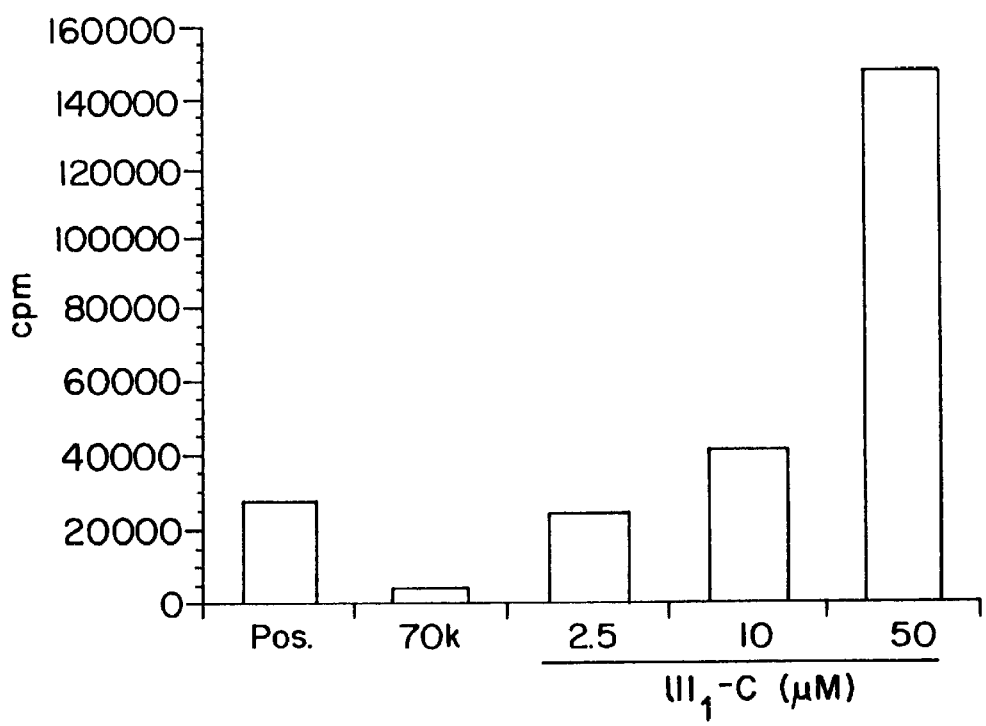
FIG. 20 illustrates the enhancement of fibronectin matrix deposition in CHO cells by the $III_1$-C polypeptide.

Semi-confluent CHO cells were treated with either III$_1$-C, or with the N-terminal 70 kDa fragment, which is already known to inhibit matrix formation. The matrix production was measured as incorporation of $^{125}$I-fibronectin into a fraction resistant to deoxycholate extraction, as described in Morla et al. (1992), supra. As shown in FIG. 20, III$_1$-C was quite effective in enhancing the deposition of fibronectin into the matrix of the CHO cell line C11. There was typically over a 5-fold induction of fibronectin matrix assembly by 50 μM III$_1$-C in the assays. The column marked Pos shows matrix production in an untreated control culture.

Thus, in addition to stimulating fibronectin-fibronectin binding and cross-linking in vitro, the III$_1$-C protein was able to enhance fibronectin matrix assembly in tissue culture cells.

EXAMPLE XIV

Inhibition of CHO Cell Migration by III$_1$-C

Figure 21A:
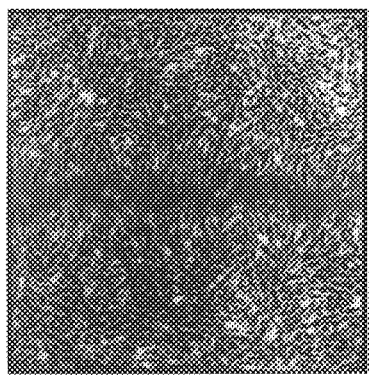
FIG. 21A shows the migration of C11 cells alone.
Figure 21B:
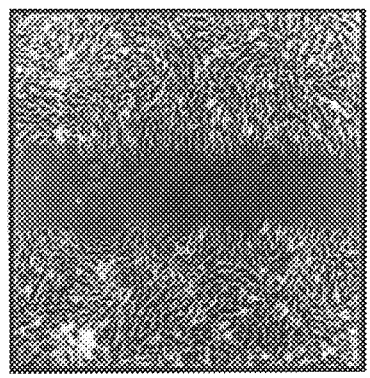
FIG. 21B shows the migration of C11 cells after the application of the $III_1$-C polypeptide.
Figure 21C:
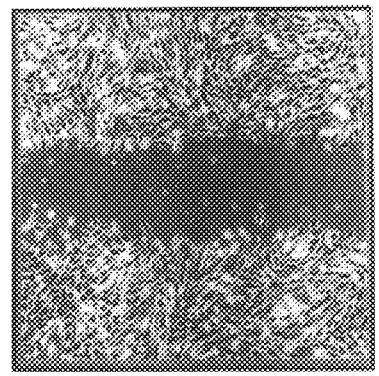
FIG. 21C shows the migration of A3 cells.

It is known from previous work (see Giancotti and Ruoslahti, (1990), supra) that there is a correlation between an increase in fibronectin matrix assembly and the decrease in tumorigenic phenotype. Since the polypeptides of the present invention including the recombinant polypeptides are able to modulate fibronectin matrix assembly, the se proteins were tested to determine if they CHO cell line, which does not overexpress $\alpha_5\beta_1$ fibronectin receptors, and is tumorigenic, was grown in the presence or absence of 50 μM III$_1$-C. As a comparison, A3 CHO cells, which do overexpress $\alpha_5\beta_1$ fibronectin receptors and are less tumorigenic, were grown in parallel. The migration of the cells was tested in an in vitro "wounding" assay as described in Example II. As shown in FIG. 21A (C11 cells) and 21C (A3 cells), A3 cells initially migrated less well than C11 cells. However, the addition of the III$_1$-C protein to C11 cells (FIG. 21B) resulted in a retardation of their migration, such that they migrated at approximately the same rate as the A3 cells (FIGS. 21B and 21C). Thus, the III$_1$-C protein which increases the fibronectin matrix assembly of these cells also decreased their rate of migration. This decreased rate of migration is a strong indication that III$_1$-C and related polypeptides can inhibit the tumorigenic phenotype of cancer cells.

The results of Examples XII through XIV show that recombinant polypeptides representing portions of the III$_1$ repeat can induce fibronectin disulfide cross-linking in vitro, can enhance fibronectin matrix assembly in tissue culture, and can inhibit cell migration in tissue culture.

While the invention has been described in detail with reference to presently preferred embodiments, it is understood that various modifications can be made without departing from the spirit of the invention. Accordingly, the invention is limited only by the following claims.

We claim:

1. A substantially purified recombinantly produced polypeptide fragment of the III$_1$ repeat (Sequence ID NO:1) of fibronectin having the ability to bind fibronectin.

2. A polypeptide according to claim 1, wherein said polypeptide fragment is III$_1$-C (Sequence ID No. 11), III$_1$-E (Sequence ID No. 12), or QE-C (Sequence ID No. 13).

3. A polypeptide according to claim 1, wherein said polypeptide fragment has the capacity to inhibit fibronectin-fibronectin binding.

4. The polypeptide of claim 3, wherein said polypeptide fragment is III$_1$-E (Sequence ID No. 12).

* * * * *

UNITED STATES PATENT AND TRADEMARK OFFICE
CERTIFICATE OF CORRECTION

PATENT NO. : 5,837,813
DATED : November 17, 1998
INVENTOR(S) : Ruoslahti et al.

It is certified that error appears in the above-identified patent and that said Letters Patent is hereby corrected as shown below:

Column 17,
Line 46, please delete "to SB" and replace with -- to 5B --.

Column 23,
Line 48, please delete "IIIT$_1$-E" and replace with -- III$_1$-E --.

Column 26,
Line 39, please delete "they CHO" and replace with -- they could modulate the tumorigenic phenotype of cells. The C11 CHO --.

Signed and Sealed this

Thirtieth Day of April, 2002

Attest:

JAMES E. ROGAN
*Attesting Officer*     *Director of the United States Patent and Trademark Office*